United States Patent
Hai et al.

(10) Patent No.: US 7,384,558 B2
(45) Date of Patent: Jun. 10, 2008

(54) COMPOSITIONS CAPABLE OF INHIBITING REACTIVE OXYGEN AND CARBONYL SPECIES

(75) Inventors: Ton That Hai, Round Lake, IL (US); Mark Nordhaus, Antioch, IL (US); Paul Sanders, Greendale, WI (US); Cong Jiang, Gurnee, IL (US); Sujatha Karoor, Lake Bluff, IL (US); Ben Melnick, Chicago, IL (US); Leo Martis, Long Grove, IL (US)

(73) Assignees: Baxter International Inc., Deerfield, IL (US); Baxter Healthcare S.A., Zurich (CH)

( * ) Notice: Subject to any disclaimer, the term of this patent is extended or adjusted under 35 U.S.C. 154(b) by 535 days.

(21) Appl. No.: 10/899,194

(22) Filed: Jul. 26, 2004

(65) Prior Publication Data
US 2006/0016752 A1   Jan. 26, 2006

(51) Int. Cl.
*B01D 61/26* (2006.01)
(52) U.S. Cl. ............ 210/647; 210/645; 210/646; 514/1; 514/458; 549/410; 549/412; 549/418; 604/29
(58) Field of Classification Search ............ 210/645, 210/646, 647, 650; 424/600; 514/1, 458; 549/410, 412, 418; 604/29
See application file for complete search history.

(56) References Cited

U.S. PATENT DOCUMENTS

| | | | |
|---|---|---|---|
| 4,344,886 A | 8/1982 | Horner et al. | |
| 5,055,598 A | 10/1991 | Ohuchida et al. | |
| 5,120,849 A | 6/1992 | Wild et al. | |
| 5,431,496 A | 7/1995 | Balteau et al. | |
| 5,508,450 A | 4/1996 | Ohuchida et al. | |
| 5,527,272 A | 6/1996 | Folden | |
| 5,668,117 A * | 9/1997 | Shapiro ............ 514/55 |
| 5,891,341 A | 4/1999 | Li et al. | |
| 5,954,958 A | 9/1999 | Folden | |
| 6,258,577 B1 | 7/2001 | Goodrich, Jr. et al. | |
| 6,277,337 B1 | 8/2001 | Goodrich, Jr. et al. | |
| 6,309,673 B1 | 10/2001 | Duponchelle et al. | |
| 6,319,243 B1 | 11/2001 | Becker et al. | |
| 6,342,500 B1 | 1/2002 | Khalifah et al. | |
| 6,436,969 B1 | 8/2002 | Khalifah et al. | |
| 6,475,434 B1 | 11/2002 | Darouiche | |
| 6,610,852 B2 | 8/2003 | Khalifah et al. | |

(Continued)

FOREIGN PATENT DOCUMENTS

EP   0387771   9/1990

(Continued)

OTHER PUBLICATIONS

Vitamin E web article, pp. 1-6 (Mar. 2007).*

(Continued)

*Primary Examiner*—John Kim
(74) *Attorney, Agent, or Firm*—Paula Kelly; Robert M. Barrett

(57) ABSTRACT

Therapeutic compositions are provided. The compositions include a single molecule that can display both antioxidant and carbonyl trapping properties. This can effectively reduce inflammation, oxidative stress and carbonyl stress, such as to prevent and/or treat cardiovascular disease and inflammatory diseases in kidney disease patients.

6 Claims, 19 Drawing Sheets

AO: Antioxidant Moiety
  1- Vitamin E
  2- Cinnamic Acid Derivative: Caffeic acid, Ferrulic Acid, Sinapic acid.
  3- Pyridoxamine
  4- Flavonoids (Hesperetin, Diosmin)
  5- Lipoic acid
  6- Natural or synthetic Antioxidants CT: Carbonyl Trapping Moiety
  1- Aminooxy Group
  2- 1,2-Aminothiol Group: Cysteine, Penicillamine L: Linker Moiety
  1- Piperazine
  2- Short Chain PEG
  3- Lysine
  4- Organic Moiety containing Positive and/or Negative Charges

U.S. PATENT DOCUMENTS

| | | | |
|---|---|---|---|
| 6,919,326 B1 | 7/2005 | Miyata | |
| 7,029,906 B2* | 4/2006 | Miyata | 435/269 |
| 2001/0051658 A1* | 12/2001 | Jacobson et al. | 514/665 |
| 2002/0037329 A1 | 3/2002 | Martis et al. | |
| 2002/0119957 A1 | 8/2002 | Khalifah et al. | |
| 2003/0004105 A1 | 1/2003 | Assaly et al. | |
| 2003/0007961 A1* | 1/2003 | Wilburn | 424/94.4 |
| 2003/0017995 A1 | 1/2003 | Khalifah et al. | |
| 2003/0065292 A1 | 4/2003 | Darouiche et al. | |
| 2003/0138501 A1 | 7/2003 | Elisabettini et al. | |
| 2004/0058850 A1* | 3/2004 | Fritz et al. | 514/1 |
| 2005/0020507 A1* | 1/2005 | Zieske et al. | 514/23 |

FOREIGN PATENT DOCUMENTS

| | | |
|---|---|---|
| EP | 0 667 140 B1 | 2/1995 |
| EP | 1 108 434 A1 | 6/2001 |
| EP | 1108434 | 6/2001 |
| JP | 03-204874 | 9/1991 |
| JP | 04-308586 | 10/1992 |
| JP | 08-337590 | 12/1996 |
| JP | 11-071273 | 3/1999 |
| WO | WO 00/33895 | 6/2000 |
| WO | WO 00/51987 | 9/2000 |
| WO | WO 01/02004 A1 | 1/2001 |
| WO | WO 00/04930 | 4/2001 |
| WO | WO 02/47677 A1 | 6/2002 |
| WO | WO 02/053094 A2 | 7/2002 |
| WO | WO 02/094179 A2 | 11/2002 |
| WO | WO 02/100455 A2 | 12/2002 |
| WO | WO 03/045448 A1 | 6/2003 |
| WO | WO 03/047567 A1 | 6/2003 |
| WO | WO 03/057226 A1 | 7/2003 |

OTHER PUBLICATIONS

Smith et al., "Improved high-performance liquid chromatographic method for artifact-free measurements of aldehydes in the presence of ozone using 2,4-dinitrophenylhydrazine," Journal of Chromatography, 483 (1989) pp. 431-436.

Foley et al., "Cardiovascular disease in chronic renal disease," American Journal of Kidney Diseases, vol. 32, No. 5, Suppl. 3 (Nov. 1998), pp. S112-S119.

Nilsson-Thorell et al., "Heat sterilization of fluids for peritoneal dialysis gives rise to aldehydes," Peritoneal Dialysis International, vol. 13 (1993) pp. 208-213.

Linden et al., "3,4-Dideoxyglucosone-3-ene (3,4-DGE): A cytotoxic glucose degradation product in fluids for peritoneal dialysis," Kidney International, vol. 62 (2002) pp. 697-703.

Witowski et al., "Prolonged Exposure to Glucose Degradation Products Impairs Viability and Function of Human Peritoneal Mesothelial Cells," J. Am. Soc. Nephrol., vol. 12 (2001) pp. 2434-2441.

Witowski et al., "Effect of Glucose Degradation Products on Human Peritoneal Mesothelial Cell Function," J. Am. Soc. Nephrol., vol. 11 (2002) pp. 729-739.

Kuroda et al., "Serum Antioxidant Activity in Uremic Patients," Nephron, vol. 41 (1985) pp. 293-298.

Aoyagi et al., "Role of active oxygen on methylguanidine synthesis in isolated rap hepatocytes," Kidney International, vol. 32, Suppl. 22 (1987) pp. S-229-S-233.

Aoyagi et al., "Artificial kidney for the treatment of redox state abnormality in renal failure," J. Artif. Organs, vol. 4 (2001) pp. 1-2.

Lameire et al., "Blood Purification," Blood Purif., vol. 17 (1999) pp. 55-57.

Haugen et al., "The Involvement of Oxidative Stress in the Progression of Renal Injury," Blood Purif., vol. 17 (1999) pp. 58-65.

Sevanian et al., "Low Density Lipoprotein (LDL) Modification: Basic Concepts and Relationship to Atherosclerosis," Blood Purif., vol. 17 (1999) pp. 66-78.

Galli et al., "Biological Effects of Oxidant Street in Haemodialysis: The Possible Roles of Vitamin E," Blood Purif., vol. 17 (1999) pp. 79-94.

Inagi et al., "Oxidative Protein Damage with Carbohydrates and Lipids in Uremia: 'Carbonyl Stress,'" Blood Purif., vol. 17 (1999) pp. 95-98.

Canaud et al., "Imbalance of Oxidants and Antioxidants in Haemodialysis Patients," Blood Purif., vol. 17 (1999) pp. 99-106.

Bonomini et al., "Surface Antigen Expression and Platelet Neutrophil Interactions in Haemodialysis," Blood Purif., vol. 17 (1999) pp. 107-117.

Tetta et al., "An Overview of Haemodialysis and Oxidant Stress," Blood Purif., vol. 17 (1999) pp. 118-126.

Wratten et al., "Haemolopodialysis," Blood Purif., vol. 17 (1999) pp. 127-133.

Wratten et al., "Uremic Ultrafiltrate Inhibits Platelet-Activating Factor Synthesis," Blood Purif., vol. 17 (1999) pp. 134-141.

Panichi et al., "Plasma C-Reactive Protein in Haemodialysis," Blood Purif., vol. 17 (1999) pp. 142-148.

Memoli et al., "Cytokine Production in Haemodialysis," Blood Purif., vol. 17 (1999) pp. 149-158.

Movilli et al. "Adequacy, Nutrition, and Biocompatibility: Their Relevance on Clinical Outcome in Haemodialysis Patients," Blood Purif., vol. 17 (1999) pp. 159-165.

Ronco et al., "New Perspectives in the Treatment of Acute Renal Failure," Blood Purif., vol. 17 (1999) pp. 166-172.

Nicoletta et al., "Antioxidant Activity Applying an Improved ABTS Radical Cation Decolorization Assay," Free Radical Biology & Medicine, vol. 26, Nos. 9/10 (1999) pp. 1231-1237.

* cited by examiner

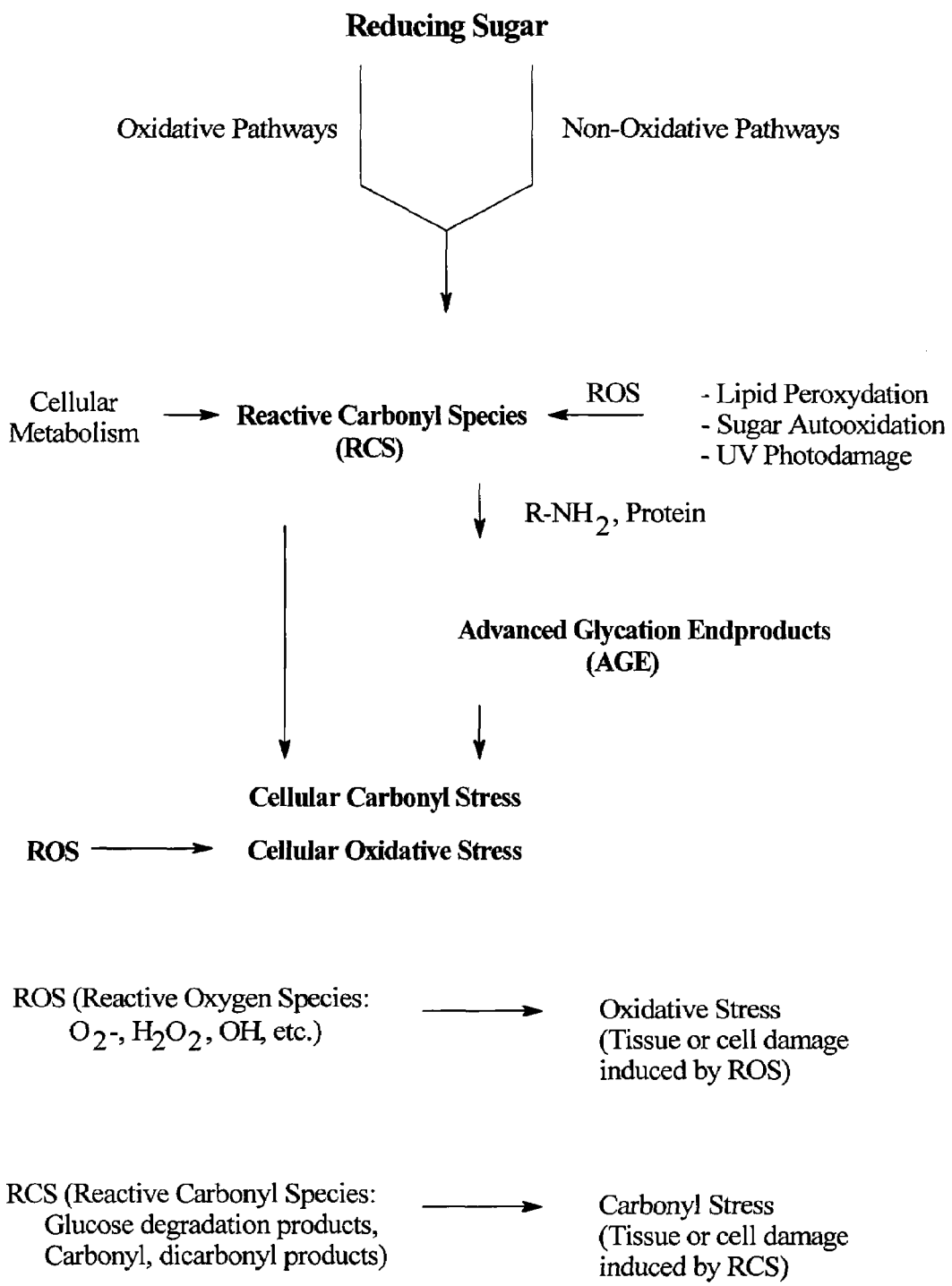

FIG. 2

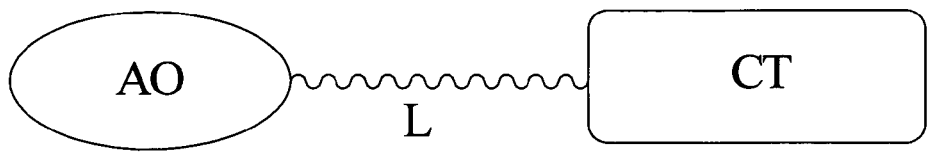

AO: Antioxidant Moiety

1- Vitamin E
    2- Cinnamic Acid Derivative: Caffeic acid, Ferrulic Acid, Sinapic acid.
    3- Pyridoxamine
    4- Flavonoids (Hesperetin, Diosmin)
    5- Lipoic acid
    6- Natural or synthetic Antioxidants

CT: Carbonyl Trapping Moiety

1- Aminooxy Group
    2- 1,2-Aminothiol Group: Cysteine, Penicillamine

L: Linker Moiety

1- Piperazine
    2- Short Chain PEG
    3- Lysine
    4- Organic Moiety containing Positive and/or Negative Charges

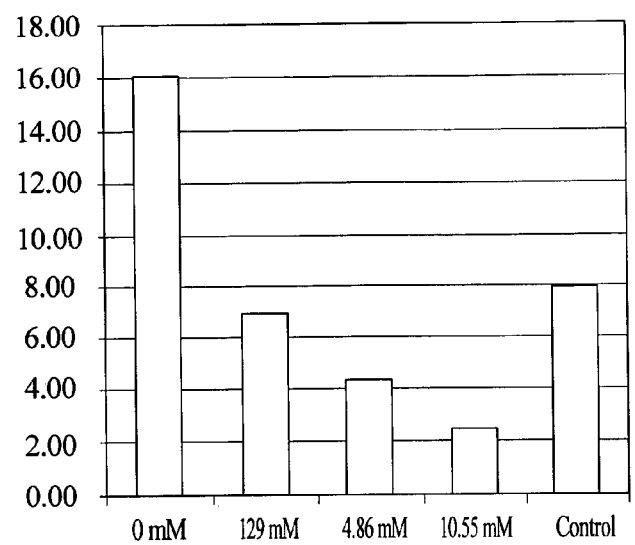
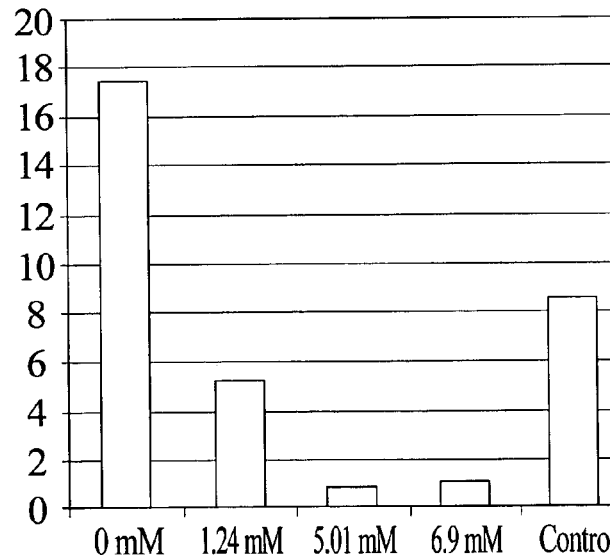

FIG. 14A
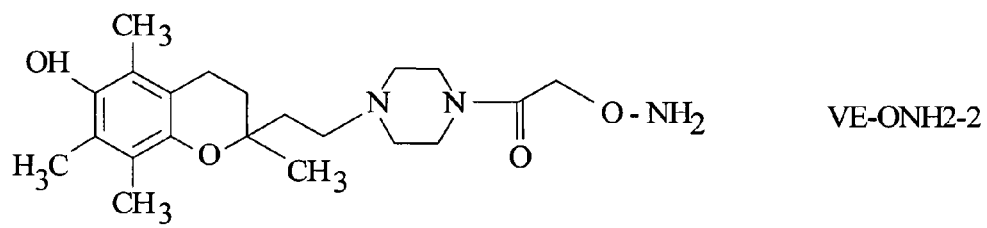 VE-ONH2-2
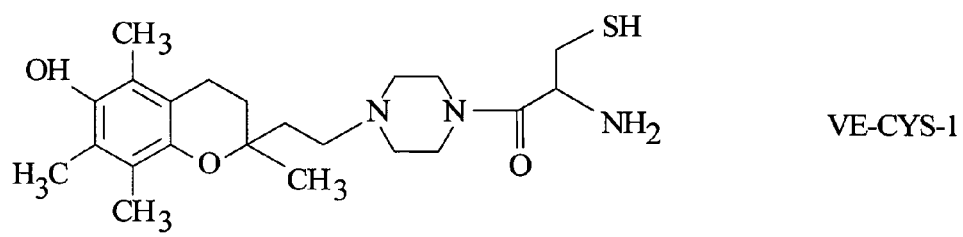 VE-CYS-1
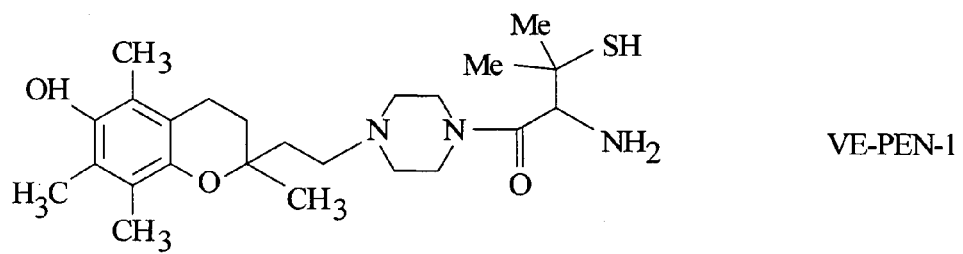 VE-PEN-1
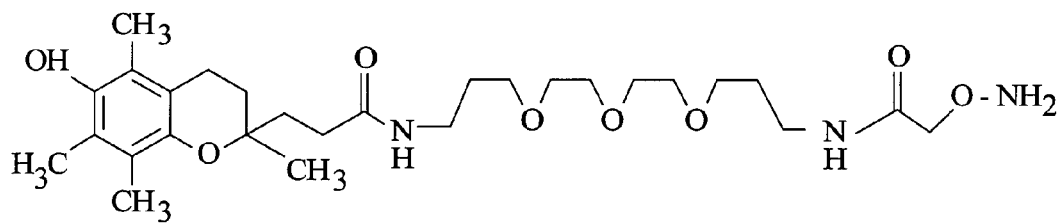
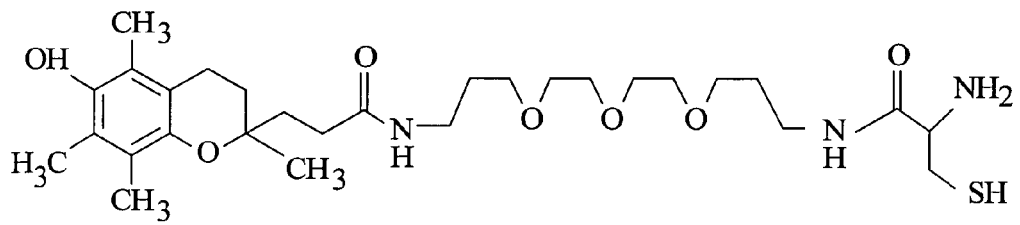
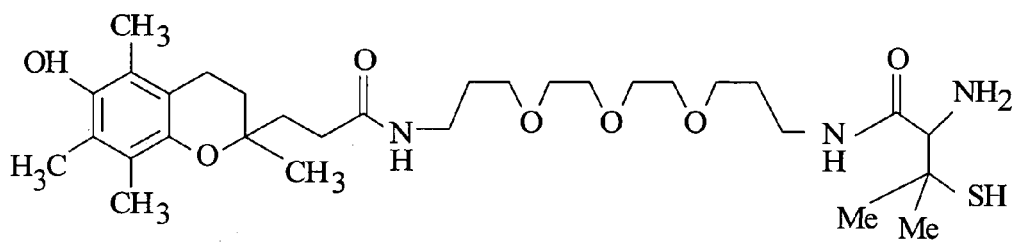

FIG. 14B
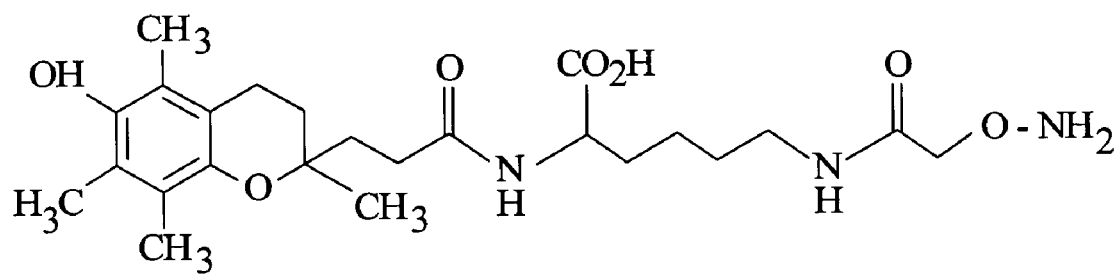
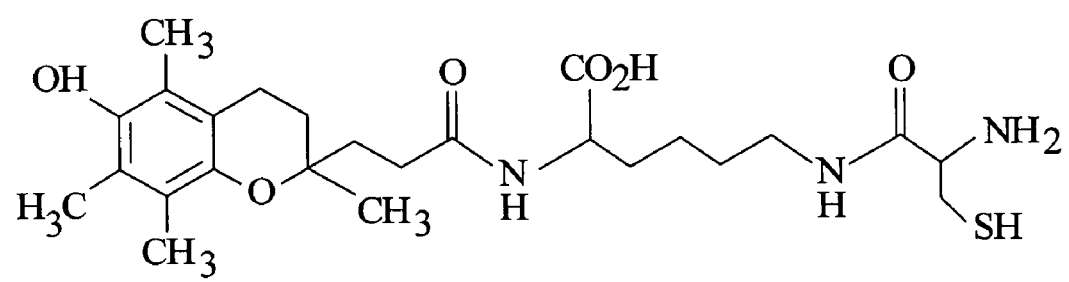
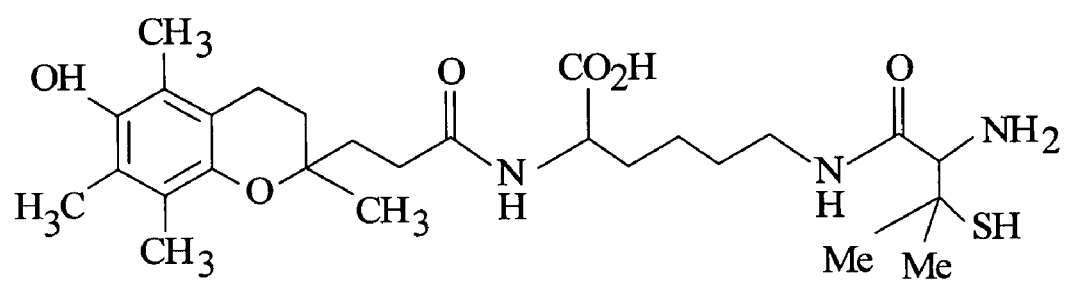
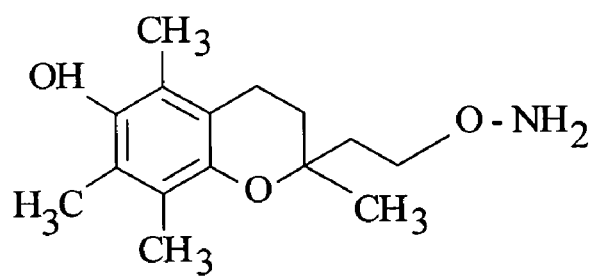 VE-ONH2-1

FIG. 14C
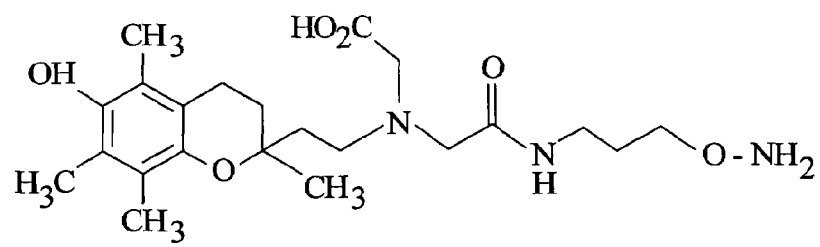
(Molecule containing Positive and Negative charges)
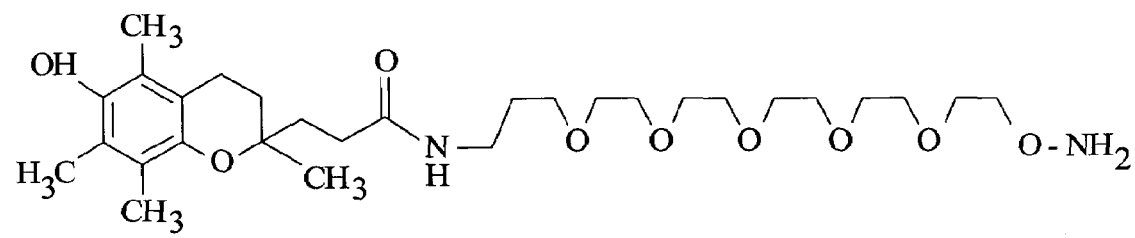
(Modecule containing PEG)
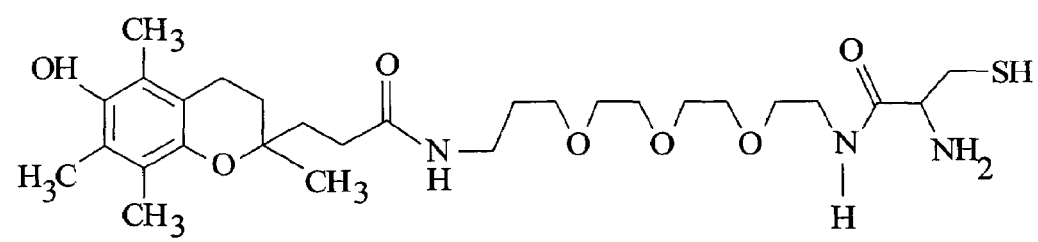
(Modecule containing PEG)

COMPOSITIONS CAPABLE OF INHIBITING REACTIVE OXYGEN AND CARBONYL SPECIES

BACKGROUND OF THE INVENTION

The present invention relates generally to medical treatments. More specifically, the present invention relates to therapeutic compositions used for medical treatment, such as dialysis therapy.

Due to disease, insult or other causes, a person's renal system can fail. In renal failure of any cause, there are several physiological derangements. The balance of water, minerals and the excretion of daily metabolic load are no longer possible in renal failure. During renal failure, toxic end products of nitrogen metabolism (e.g., urea, creatinine, uric acid, and the like) can accumulate in blood and tissues.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving. One who has failed kidneys could not continue to live without replacing at least the filtration functions of the kidneys.

Hemodialysis, hemofiltration and peritoneal dialysis are three types of dialysis therapies generally used to treat loss of kidney function. Hemodialysis treatment removes waste, toxins and excess water directly from the patient's blood. The patient is connected to a hemodialysis machine, and the patient's blood is pumped through the machine. For example, needles or catheters can be inserted into the patient's veins and arteries to connect the blood flow to and from the hemodialysis machine. As blood passes through a dialyzer in the hemodialysis machine, the dialyzer removes the waste, toxins and excess water from the patient's blood and returns the blood to infuse back into the patient. A large amount of dialysate, for example about 90-120 liters, is used by most hemodialysis machines to dialyze the blood during a single hemodialysis therapy. The spent dialysate is then discarded. Hemodialysis treatment lasts several hours and is generally performed in a treatment center about three times per week.

Hemofiltration is a convection-based blood cleansing technique. Blood access can be venovenous or arteriovenous. As blood flows through the hemofilter, a transmembrane pressure gradient between the blood compartment and the ultrafiltrate compartment causes plasma water to be filtered across the highly permeable membrane. As the water crosses the membrane, it convects small and large molecules across the membrane and thus cleanses the blood. An excessive amount of plasma water is eliminated by filtration. Therefore, in order to keep the body water balanced, fluid must be substituted continuously by a balanced electrolyte solution (replacement or substitution fluid) infused intravenously. This substitution fluid can be infused either into the arterial blood line leading to the hemofilter (predilution) or into the venous blood line leaving the hemofilter.

Peritoneal dialysis utilizes a sterile dialysis solution or "dialysate", which is infused into a patient's peritoneal cavity and into contact with the patient's peritoneal membrane. Waste, toxins and excess water pass from the patient's bloodstream through the peritoneal membrane and into the dialysate. The transfer of waste, toxins, and excess water from the bloodstream into the dialysate occurs due to diffusion and osmosis during a dwell period as an osmotic agent in the dialysate creates an osmotic gradient across the membrane. The spent dialysate is later drained from the patient's peritoneal cavity to remove the waste, toxins and excess water from the patient.

There are various types of peritoneal dialysis therapies, including continuous ambulatory peritoneal dialysis ("CAPD") and automated peritoneal dialysis. CAPD is a manual dialysis treatment, in which the patient connects the catheter to a bag of fresh dialysate and manually infuses fresh dialysate through the catheter or other suitable access device and into the patient's peritoneal cavity. The patient disconnects the catheter from the fresh dialysate bag and allows the dialysate to dwell within the cavity to transfer waste, toxins and excess water from the patient's bloodstream to the dialysate solution. After a dwell period, the patient drains the spent dialysate and then repeats the manual dialysis procedure. Tubing sets with "Y" connectors for the solution and drain bags are available that can reduce the number of connections the patient must make. The tubing sets can include pre-attached bags including, for example, an empty bag and a bag filled with dialysate.

In CAPD, the patient performs several drain, fill, and dwell cycles during the day, for example, about four times per day. Each treatment cycle, which includes a drain, fill and dwell, takes about four hours.

Automated peritoneal dialysis is similar to continuous ambulatory peritoneal dialysis in that the dialysis treatment includes a drain, fill, and dwell cycle. However, a dialysis machine automatically performs three or more cycles of peritoneal dialysis treatment, typically overnight while the patient sleeps.

With automated peritoneal dialysis, an automated dialysis machine fluidly connects to an implanted catheter. The automated dialysis machine also fluidly connects to a source or bag of fresh dialysate and to a fluid drain. The dialysis machine pumps spent dialysate from the peritoneal cavity, through the catheter, to the drain. The dialysis machine then pumps fresh dialysate from the dialysate source, through the catheter, and into the patient's peritoneal cavity. The automated machine allows the dialysate to dwell within the cavity so that the transfer of waste, toxins and excess water from the patient's bloodstream to the dialysate solution can take place. A computer controls the automated dialysis machine so that the dialysis treatment occurs automatically when the patient is connected to the dialysis machine, for example, when the patient sleeps. That is, the dialysis system automatically and sequentially pumps fluid into the peritoneal cavity, allows for dwell, pumps fluid out of the peritoneal cavity, and repeats the procedure.

Several drain, fill, and dwell cycles will occur during the treatment. Also, a smaller volume "last fill" is typically used at the end of the automated dialysis treatment, which remains in the peritoneal cavity of the patient when the patient disconnects from the dialysis machine for the day. Automated peritoneal dialysis frees the patient from having to manually perform the drain, dwell, and fill steps during the day.

In general, standard peritoneal dialysis solutions contain dextrose at a concentration of 1.5% to 4.25% by weight to effect transport of water and metabolic waste products across the peritoneal membrane. Dextrose is generally recognized as a safe and effective osmotic agent, particularly for short dwell exchanges.

Although the use of dialysis, and other methods for treating patients with renal disease, provide treatments that allow patients with renal failure to survive, currently used compositions and methods may not provide all necessary therapeutic agents necessary to address renal failure and other associated disease.

For example, cardiovascular mortality in kidney disease patients is several fold higher than in the general population. For example, cardiac mortality for dialysis patients aged 45 years or younger is more than 100-fold greater than in the general population. Even in the elderly, cardiovascular mortality is at least five fold higher in the end-stage renal disease population than in the general population. See, for example, Foley R, Parfrey P S, Sarnak M J: Clinical epidemiology of cardiovascular disease in chronic renal disease. Am J Kidney Dis 32:S112-S119, 1998. In addition, the traditional risk factors for cardiovascular mortality in the general population such as hypertension and hypercholesterolemia are not good predictors in dialysis patients while non-traditional risk factors such as markers of inflammation and nutrition are good predictors. A line of evidence suggests that oxidative and carbonyl stress that are elevated in dialysis patients play a major role in producing inflammatory cytokines. In this regard, it is well known that bioincompatible glucose degradation products ("GDPs") in fluids for peritoneal dialysis are produced during heat sterilization and storage. Many GDPs are highly reactive carbonyl species ("RCS") towards cellular targets, and are toxic both in a general sense and through interactions with proteins and nucleic acids. In addition, carbonyl compounds are elevated in dialysis patients due to abnormal metabolism and decreased clearance.

Oxidative stress is the result of an imbalance between reactive oxygen species ("ROS") production and antioxidant defense mechanisms. It has been reported that oxidative stress is increased in patients with renal failure. The antioxidant system is severely impaired in uremic patients and is gradually altered with the degree of renal failure.

The effects of ROSs and RCSs are summarized in FIG. 1. The use of carbonyl trapping agents to eliminate RCSs has been generally reported. Antioxidants, in general, have also been used to reduce oxidative stress in dialysis patients. They have been used independent of each other.

A need, therefore, exists to provide improved therapeutic compositions that can inhibit both reactive carbonyl species and reactive oxygen species, such as in kidney disease patients.

SUMMARY OF THE INVENTION

The present invention generally relates to therapeutic compositions. More specifically, the compositions can be effectively used to inhibit the activity of reactive oxygen and reactive carbonyl species. This can provide for a reduction in inflammation, oxidative stress, carbonyl stress and the like to a patient that has been administered the composition during therapy, such as dialysis therapy. The single molecule can include an antioxidant moiety, a carbonyl trapping moiety, and a linker moiety. The linker moiety joins the antioxidant moiety and the carbonyl trapping moiety. The composition can be provided in any suitable form, such as in solution form, an orally administered product and the like.

In an embodiment, the present invention provides a composition that includes a single molecule capable of inhibiting a reactive oxygen species and a reactive carbonyl species.

In an embodiment, the linker molecule determines the physico-chemical properties such as aqueous solubility, hydrophilic-lipophilic balance and the like. The linker moiety can include, for example, piperazine, poly(ethylene glycol), lysine, an organic moiety containing positive charges, an organic moiety containing negative charges, an organic moiety containing negative and positive charges and combinations thereof.

In an embodiment, the antioxidant moiety includes, for example, vitamin E, cinnamic acid derivatives, pyridoxamine, flavonoids, lipoic acid, antioxidants, natural antioxidants, synthetic antioxidants, derivatives thereof, the like and combinations thereof.

In an embodiment, the carbonyl trapping moiety includes, for example, an aminooxy group and a 1,2-aminothiol group such as cysteine group, penicillamine group and combinations thereof.

In an embodiment, the single molecule includes a vitamin E derivative. The vitamin E derivative can be composed of a vitamin E-based moiety and a carbonyl trapping functional group that are joined by a linker moiety. Alternatively, the vitamin E derivative can include a vitamin E-based compound that has been modified in water soluble form.

In another embodiment, a dialysis solution is provided. The dialysis solution includes a therapeutically effective amount of a composition capable of inhibiting a reactive oxygen species and a reactive carbonyl species. The composition, in an embodiment, includes an antioxidant moiety, a carbonyl trapping moiety, and a linker moiety that joins the antioxidant moiety and the carbonyl trapping moiety to form a single molecule.

In a further embodiment, a two part peritoneal dialysis solution is provided. The two part dialysis solution includes a first part including an osmotic agent; and a second part including a buffer. The first part and the second part are admixed prior to infusion into a patient wherein at least one of the first part and the second part includes a therapeutically effective amount of a composition capable of inhibiting a reactive carbonyl species and a reactive oxygen species.

In yet another embodiment, a method of producing a composition is provided. The method includes preparing a vitamin E-based compound; and processing the vitamin E-based compound to produce a single molecule that is capable of inhibiting a reactive oxygen species and a reactive carbonyl species. In an embodiment, the composition includes 2-(6-hydroxy-2,5,7,8-tetramethylchroman-2-yl)-1-(aminoxy)ethane; N-[2-(6-hydroxy-2,5,7,8-tetramethyl-chroman-2-yl)ethyl]-N'-(aminoacetyl)-piperazine; N-[2-(6-hydroxy-tetramethylchroman-2-yl)ethyl]-N'-(cysteinyl)-piperazine; N-[2-(6-hydroxy-tetramethylchroman-2-yl)ethyl]-N'-(penicillamyl)-piperazine, derivatives thereof, the like and combinations thereof. A therapeutically effective amount of the composition can be added to a dialysis solution thereby forming a ready-to-use dialysis solution, wherein the ready-to-use dialysis solution can include a hemodialysis solution, a hemofiltration solution, a hemodiafiltration solution, a peritoneal dialysis solution and the like.

In still yet another embodiment, a method of providing dialysis to a patient is provided. The method includes providing a dialysis solution that includes a therapeutically effective amount of a composition wherein the composition is capable of inhibiting a reactive oxygen species and a reactive carbonyl species; and using the dialysis solution during dialysis. The patient can be provided dialysis, such as hemodialysis, hemofiltration, hemodiafiltration, peritoneal dialysis and the like.

In a further embodiment, a method of reducing inflammation and oxidative stress in a kidney disease patient is provided. The method includes providing a dialysis solution wherein the dialysis solution includes a therapeutically effective amount of a composition that is capable of inhibiting a reactive oxygen species and a reactive carbonyl species; and using the dialysis solution to administer dialysis to the patient.

In yet a further embodiment, the present invention provides a method of reducing systemic inflammation in a patient. The method includes providing a composition that is capable of inhibiting a reactive oxygen species and a reactive carbonyl species; and administering the composition to the patient in a therapeutically effective amount to reduce systemic inflammation. The composition can be administered via an oral route, an intravenous route, a subcutaneous route, an intramuscular route, the like and combinations thereof. The composition can be used to treat an inflammatory disease.

An advantage of the present invention is to provide improved therapeutic compositions.

Another advantage of the present invention is to provide improved methods of making and using therapeutic compositions that are capable of inhibiting reactive oxygen species and reactive carbonyl species.

Yet another advantage of the present invention is to provide improved dialysis solutions that include therapeutic compositions.

Still yet another advantage of the present invention is to provide improved methods of performing dialysis that include administering therapeutic compositions that display both antioxidant and carbonyl trapping properties.

A further advantage of the present invention is to inhibit the activity of reactive carbonyl species and reactive oxygen species during dialysis therapy.

A still further advantage of the present invention is to reduce inflammation and oxidative stress in kidney disease patients.

Additional features and advantages of the present invention are described in, and will be apparent from, the following Detailed Description of the Invention and the figures.

BRIEF DESCRIPTION OF THE DRAWINGS

FIG. 1 is a schematic representation of the formation of ROSs, RCSs and cellular effects thereof.

FIG. 2 is a schematic representation of the chemical structure of the therapeutic compositions according to an embodiment of the present invention.

FIGS. 10A-10E are graphical representations of the carbonyl trapping properties of therapeutic compositions according to various embodiments of the present invention.

FIGS. 14A-14C illustrate chemical formulas that represent therapeutic compositions according to various embodiments of the present invention.

DETAILED DESCRIPTION OF THE INVENTION

The present invention generally relates to therapeutic compositions. More specifically, the present invention relates to therapeutic compositions that have both antioxidant and carbonyl trapping properties. In this regard, the therapeutic compositions can be effectively utilized to inhibit the activity of reactive oxygen species and reactive carbonyl species. This can provide a therapeutically effective reduction of inflammation and oxidative stress to a patient in need and/or at risk of same, such as during dialysis therapy.

In general, the compositions include a single molecule that has the ability to inhibit both reactive oxygen species and reactive carbonyl species. In an embodiment, the single molecule includes an antioxidant moiety, a carbonyl trapping moiety and a linker moiety that joins the antioxidant moiety and the carbonyl trapping moiety. A schematic representation of the single molecule with the antioxidant moiety, carbonyl trapping moiety and linker moiety is illustrated in FIG. 2.

The different component parts (e.g., antioxidant moiety, carbonyl trapping moiety and linker moiety) of the single molecule structure can include a variety of different and suitable materials. In an embodiment, the antioxidant moiety includes vitamin E, cinnamic acid derivatives including caffeic acid, ferrulic acid and sinapic acid, pyridoxamine, flavonoids, including hesperetin and diosmin, lipoic acid, derivatives thereof the like and combinations thereof. The linker moiety, for example, includes piperazine, poly(ethylene glycol), lysine, an organic moiety containing positive charges, an organic moiety containing negative changes, an organic moiety containing positive and negative changes, derivatives thereof, the like and combinations thereof.

Figure 3:
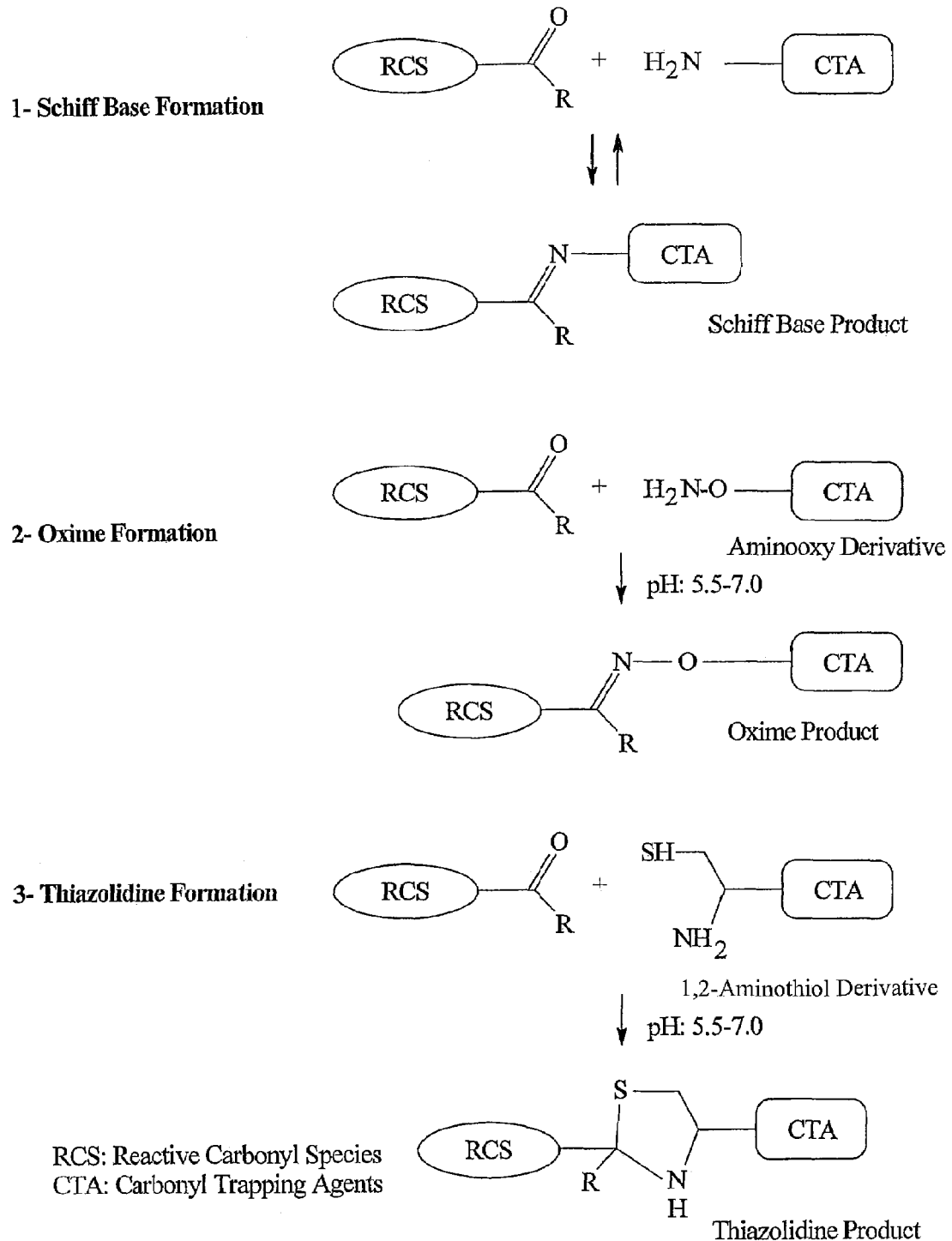
FIG. 3 is a schematic representation of the reaction pathway of carbonyl trapping agents according to an embodiment of the present invention.

The carbonyl trapping moiety, in an embodiment, includes an aminooxy group, a 1,2-aminothiol group such as cysteine group, penicillamine group, derivatives thereof, the like and combinations thereof. The carbonyl trapping moiety or agent can act to bind the reactive carbonyl species based on a number of different mechanisms depending on the carbonyl trapping agent as illustrated in FIG. 3. For example, an amine group can bind the reactive carbonyl species via the formation of a Schiff Base Product; an aminooxy derivative can bind the reactive carbonyl species via the formation of an Oxime Product; and a 1,2-aminothiol derivative can bind the reactive carbonyl species via the formation of a Thiazolidine Product.

As previously discussed, the antioxidant and carbonyl trapping agents are joined together via a linker molecule to form a single molecule that has both antioxidant and carbonyl trapping properties. For example, the single molecule of the present invention can include a vitamin E derivative that is composed of a vitamin E compound that is joined to the carbonyl trapping moiety via the linker moiety or agent. Alternatively, the vitamin E derivative can include a vitamin E compound that has been modified to a water-soluble form. Examples of a variety of different vitamin E derivatives that are illustrative of the present invention are shown in FIGS. 14A, 14B and 14C. Preferable examples of vitamin E derivatives according to an embodiment include 2-(6-hydroxy-2,5,7,8-tetramethylchroman-2-yl)-1-(aminoxy) ethane; N-[2-(6-hydroxy-2,5,7,8-tetramethylchroman-2-yl)ethyl]-N'-(aminoacetyl)-piperazine; N-[2-(6-hydroxy-tetramethylchroman-2-yl)ethyl]-N'-(cysteinyl)-piperazine; N-[2-(6-hydroxy-tetramethylchroman-2-yl)ethyl]-N'-(penicillamyl)-piperazine, derivatives thereof, the like, and combinations thereof.

Examples of therapeutic compositions and methods of preparing same are provided below without limitation in accordance with various embodiments of the present invention.

SYNTHESIS AND TEST PROCEDURES

Target vitamin E derivatives were synthesized as described below in greater detail and as identified as compounds VE-ONH2-1, VE-ONH2-2, VE-CYS-1, VE-PEN-1 pursuant to various embodiments of the present invention. Tests were then conducted to evaluate the antioxidant and carbonyl trapping properties of these compounds as further described below and in accordance with an embodiment of the present invention.

Figure 4:
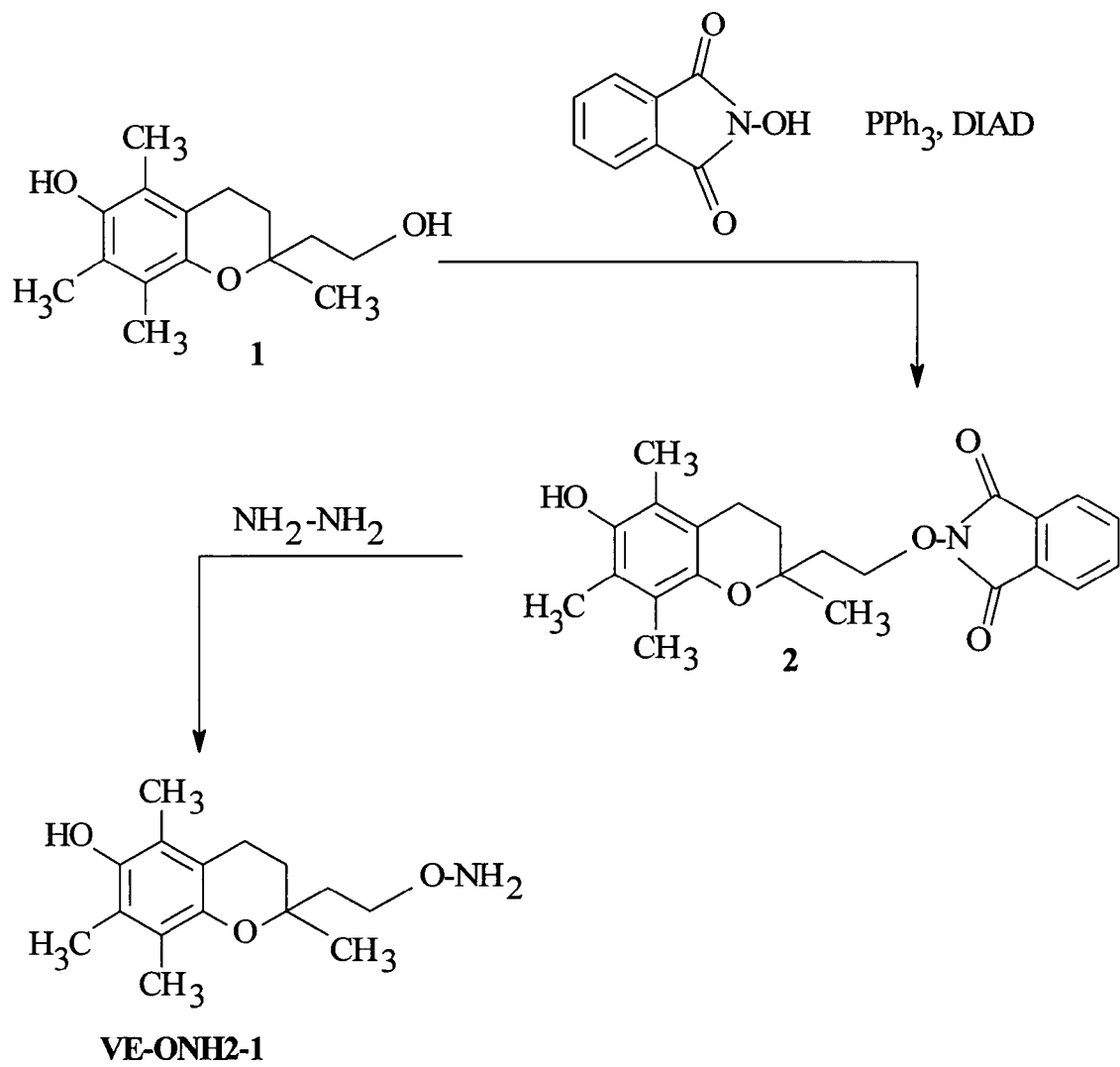
FIG. 4 is a schematic representation of a synthesis procedure associated with a therapeutic composition according to an embodiment of the present invention.

Synthesis of VE-ONH2-1: The synthesis of VE-ONH2-1 is summarized in Scheme 1 as illustrated in FIG. 4. The starting chroman (compound 1) was prepared according to the procedure disclosed in U.S. Pat. No. 4,344,886, the disclosure of which is herein incorporated by reference. Subsequent conversion of the 2-hydroxyethyl group of compound 1 to the phthaloyl aminooxy functionality in compound 2 was performed under Mitsunobu conditions employing N-hydroxyphthalimide, diisopropyl azodicarboxylate (DIAD) and $PPh_3$ at −20° C. Deprotection of compound 2 with hydrazine afforded the target product VE-ONH2-1, as described in further detail below.

Figure 5:
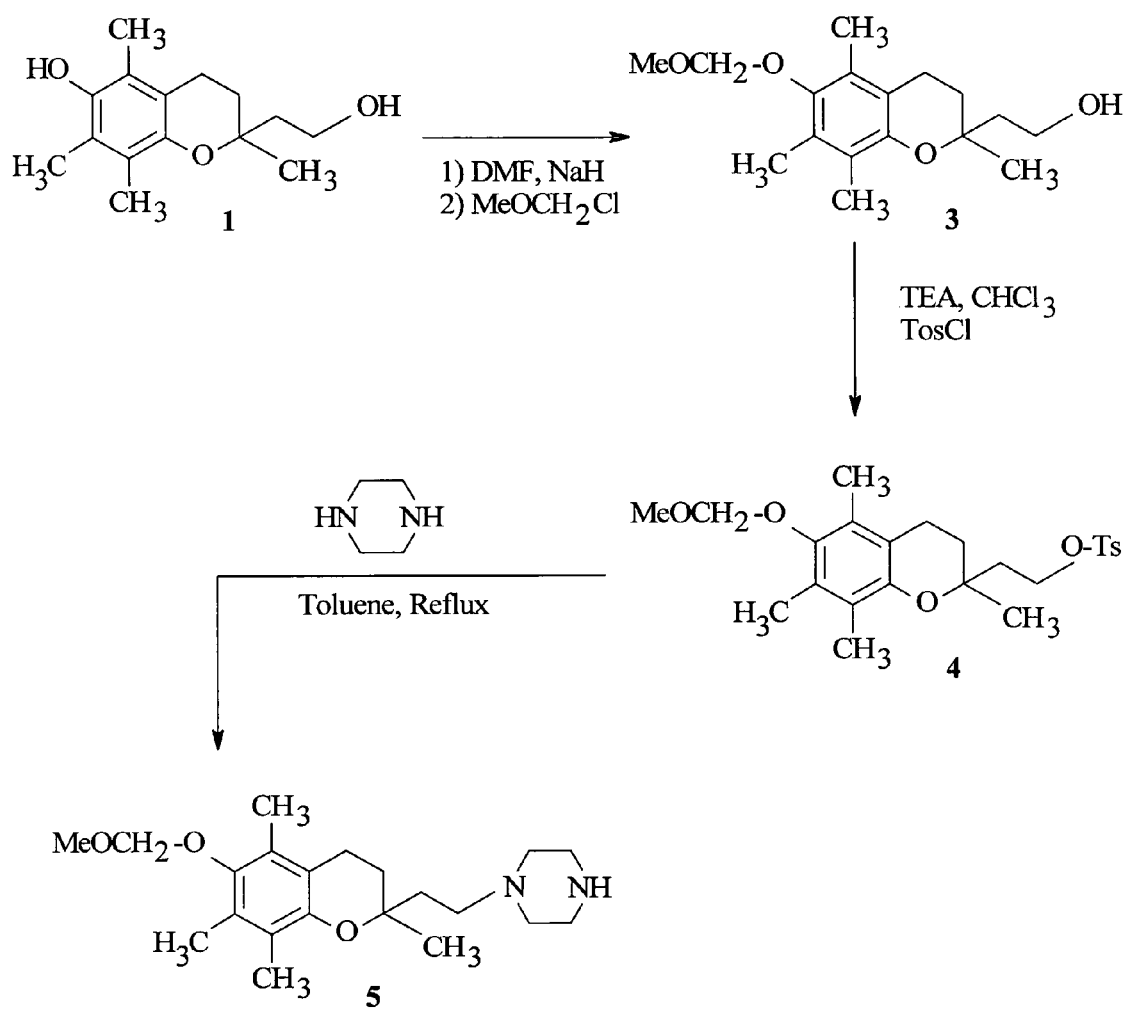
FIG. 5 is a schematic representation of a synthesis procedure associated with a therapeutic composition according to an embodiment of the present invention.

Synthesis of INTERMEDIATE (compound 5): The intermediate (compound 5) was synthesized according to Scheme 2 as illustrated in FIG. 5. Treatment of chroman (compound 1) with NaH in DMF followed by chloromethyl methyl ether gave chroman (compound 3). The 2-hydroxyethyl group of compound 3 was converted to a 2-ethyl p-toluenesulfonate group by reaction of compound 3 with p-toluenesulfonyl chloride in the presence of triethylamine in chloroform. Subsequent reaction of compound 4 with excess of piperazine (2 equivalents) produced the intermediate (compound 5).

Figure 6:
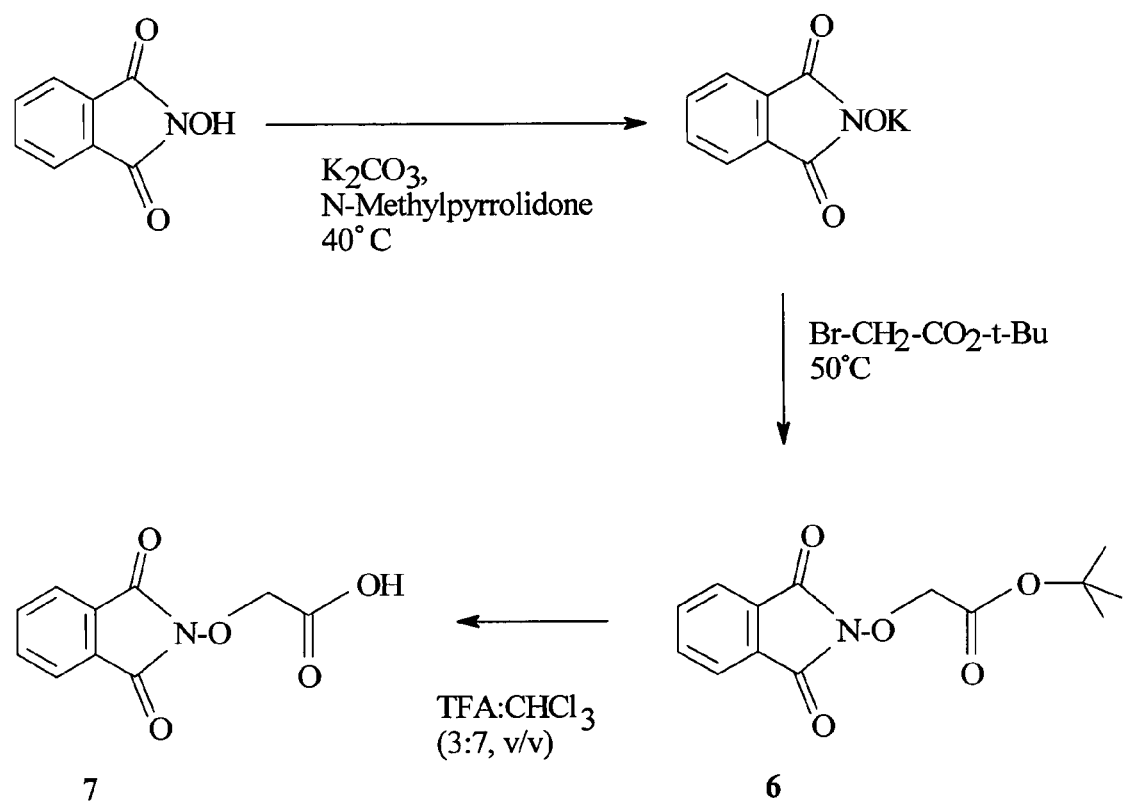
FIG. 6 is a schematic representation of a synthesis procedure associated with a therapeutic composition according to an embodiment of the present invention.

Synthesis of INTERMEDIATE (compound 7): The synthesis of intermediate (compound 7) is summarized in Scheme 3 as illustrated in FIG. 6. N-Hydroxyphthalimide was converted to its potassium salt by reaction with $K_2CO_3$ in N-methylpyrrolidone at 40° C. Subsequent treatment of the N-hydroxyphthalimide potassium with tert-butyl bromoacetate at 50° C. gave tert-butyl phthalimidooxyacetate (compound 6) in 91% yield. Removal of the tert-butyl group from compound 6 with $TFA/CHCl_3$ produced phthalimidooxyacetic acid (compound 7) in quantitative yield.

Figure 7:
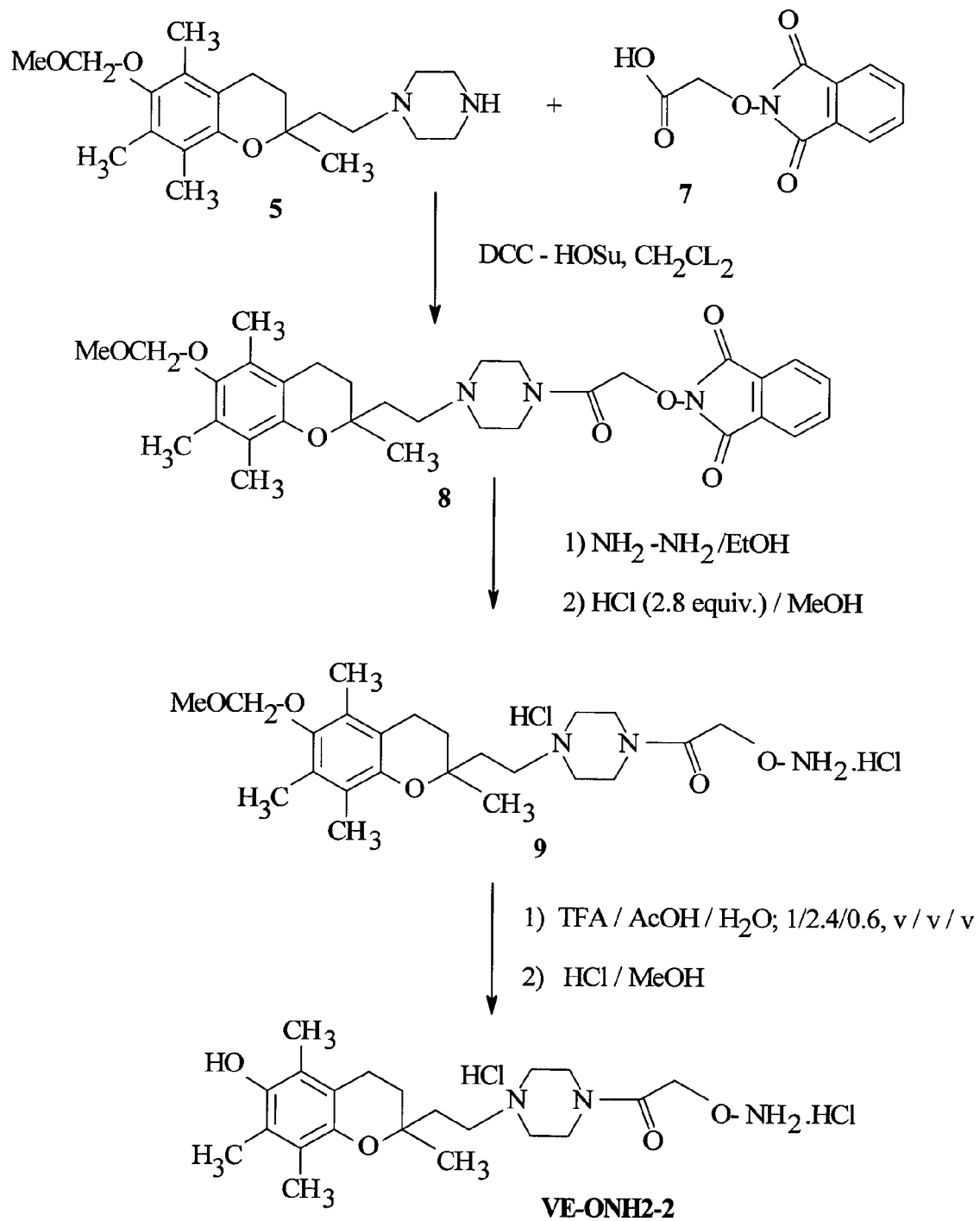
FIG. 7 is a schematic representation of a synthesis procedure associated with a therapeutic composition according to an embodiment of the present invention.

Synthesis of VE-ONH2-2: The synthesis of VE-ONH2-2 is summarized in Scheme 4 as illustrated in FIG. 7. Condensation of chroman (compound 5) with compound 7 in the presence of DCC/HOSu in methylene chloride yielded compound 8 containing two protecting groups: methoxymethyl for protecting the phenol functionality and phthalimide for protecting the oxyamine functionality. Thus, the total deprotection of compound 8 to obtain VE-ONH2-2 was completed as follows. The phthalimide group was removed first by hydrazine to give compound 9, followed by a treatment of compound 9 with $TFA/AcOH/H_2O$ (1/2.4/0.6, v/v/v) to remove the methoxymethyl group. The product VE-ONH2-2 obtained by this route was contaminated with a small amount of product which is an adduct of VE-ONH2-2 with formaldehyde via the oxyamine group. The formaldehyde was formed by the decomposition of the methoxymethyl group during the deprotection.

Figure 8:
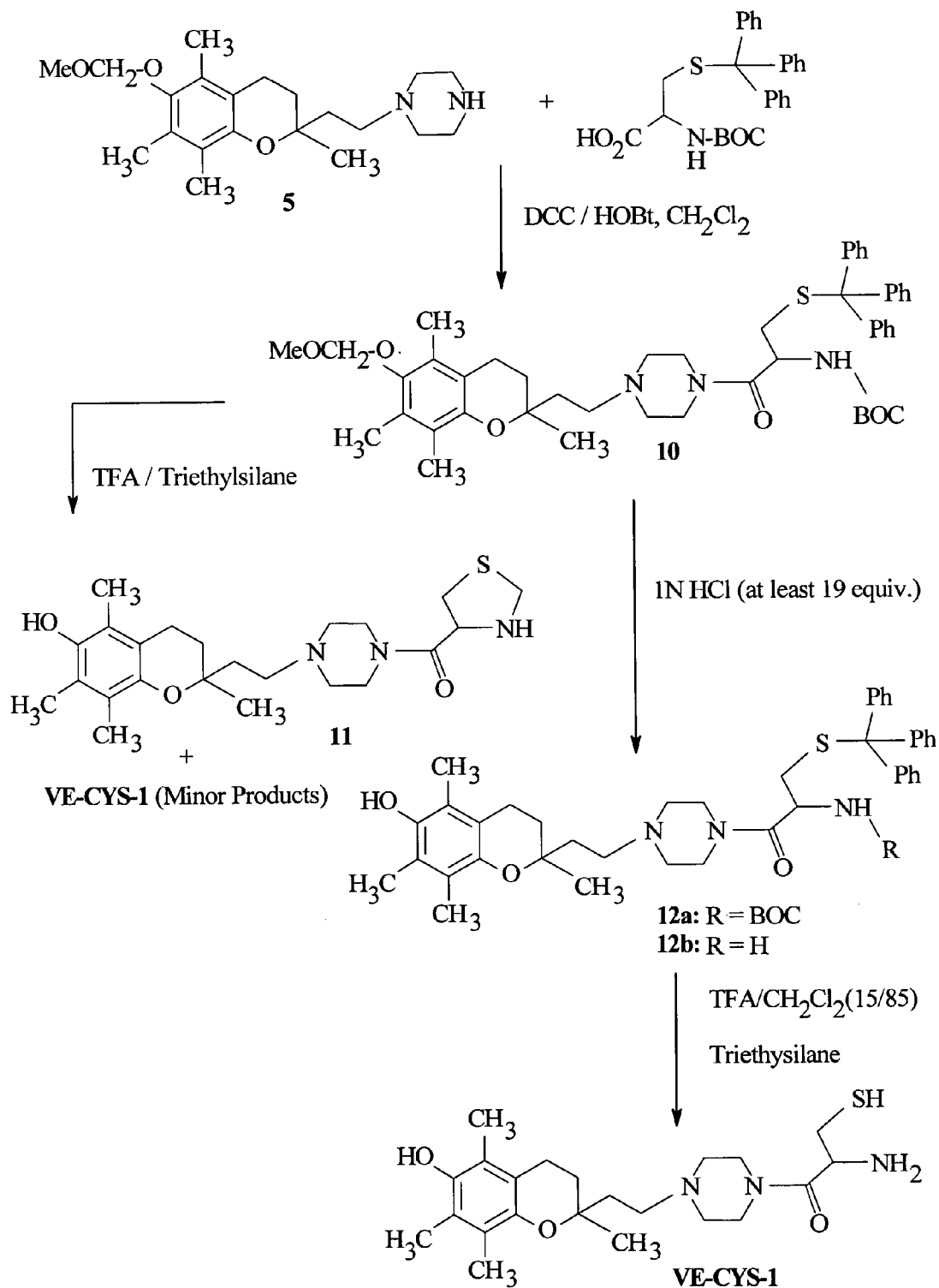
FIG. 8 is a schematic representation of a synthesis procedure associated with a therapeutic composition according to an embodiment of the present invention.

Synthesis of VE-CYS-1: The synthesis of VE-CYS-1 is summarized in Scheme 5 as illustrated in FIG. 8. Condensation of compound 5 with N-Boc-S-trityl-cysteine in methylene chloride in the presence of DCC/HOBt gave compound 10 in 81% yield. Treatment of compound 10 with TFA for 5 minutes followed by triethylsilane gave a product mixture containing compound 11 as a major product and VE-CYS-1 as a minor product. These products were identified by MS. The presence of compound 11 was due to the further reaction of VE-CYS-1 with formaldehyde derived from the decomposition of the methoxymethyl group in TFA. To avoid the formation of compound 11, the deprotection of compound 10 was completed in two steps. In the first step, the methoxymethyl group was completely removed and the BOC group was partially removed by using 1 N HCl (at least 19 equivalents of HCl); in the second step, the isolated crude product in step 1 was treated with $TFA/CH_2Cl_2$ followed by triethylsilane to give the target product VE-CYS-1 in 78% yield from compound 10.

Figure 9:
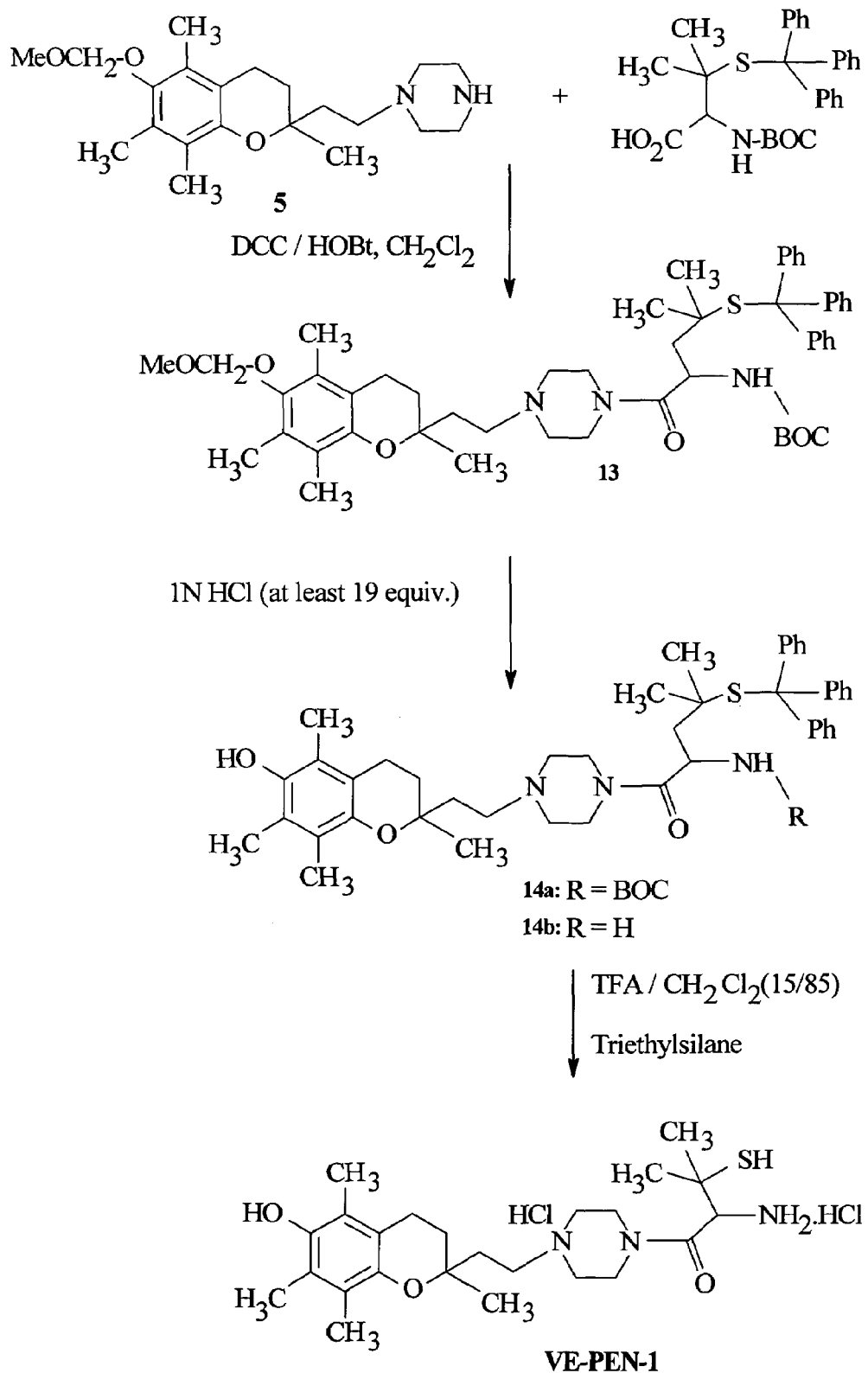
FIG. 9 is a schematic representation of a synthesis procedure associated with a therapeutic composition according to an embodiment of the present invention.

Synthesis of VE-PEN-1: The synthesis of VE-PEN-1 is summarized in Scheme 6 as shown in FIG. 9. Condensation of compound 5 with N-BOC-S-trityl-penicillamine in methylene chloride in the presence of DCC/HOBt gave compound 13 in 80% yield. Deprotection of compound 13 was completed in two steps. In the first step, the methoxymethyl group was completely removed and the BOC group was partially removed by using HCl-MeOH (1 N); in the second step, the isolated crude product (a mixture of compounds 14a and 14b) from step 1 was treated with $TFA/CHCl_3$ followed by triethylsilane to give the target product VE-PEN-1 in 80% yield.

Synthesis of 2-(6-Hydroxy-2,5,7,8-tetramethylchroman-2-yl)-1-(phthalimidooxy) ethane (compound 2): To a mixture of compound 1 (3.5 g, 14 mmole), N-hydroxyphthalimide in (2.85 g, 17.5 mmole) and $PPh_3$ (4.77 g, 18.2 mmole) in THF (50 ml) cooled to −20° C. in a dry ice and ethanol bath, diisopropyl azodicarboxylate (DIAD) (3.67 g, 18.2 mmole) was added, as illustrated in FIG. 4. The mixture was stirred at room temperature for one hour. The solvents were evaporated to dryness and the residue was dissolved in EtOAc (250 ml). DI water (5×200 ml) was used to wash the organic layer and two layers were separated. The organic layer was evaporated to dryness to give a white glass product which was purified by a silica gel column with hexane and ethyl acetate (3/1) as solvent. The residue obtained after elimination of solvent from the chromatography fractions was dried under high vacuum to give a yellow solid (compound 2) (2.4 g, 44%). The compound was characterized with nuclear magnetic resonance and mass spectrometry as follows: 1) C-NMR (CDCl$_3$): 11.61, 12.14, 12.56, 20.98, 24.41, 32.45, 37.75, 73.60, 75.31, 117.47, 118.9, 121.5, 123.04, 123.84, 129.28 134.81, 145.22, 145.29, 164.03 ppm; 2) H-NMR (CDCl$_3$): 1.34 (s, 3H), 1.6 (b, 1 OH), 1.90 (m, 2H), 2.07 (s, 3H), 2.09 (s, 3H), 2.12 (s, 3H), 2.07-2.18 (m, 2H) 2.64 (t, 2H), 4.15 (b, 1 OH), 4.4 (m, 1H), 4.47 (m, 1H), 7.74 (m, 2H), 7.82 (m, 2H) ppm; and 3) MS (ESI): 369.3 [M+H]$^+$, 418.2 [M+Na]$^+$.

Synthesis of 2-(6-Hydroxy-2,5,7,8-tetramethylchroman-2-yl)-1-(aminooxy)ethane (VE-ONH2-1): Compound 2 (1.9 g, 4.8 mmole) was dissolved in ethanol (60 ml) and hydrazine (4.0 g, 125 mmole) was added as further illustrated in FIG. 4. The mixture was stirred at room temperature overnight and the white solid was removed by filtration. The filtrate was evaporated to dryness, and the residue was dissolved in deionized (DI) water (100 ml). Chloroform (100 ml) was used to extract the product from DI water. The organic layer was washed by DI water (2×100 ml) and was evaporated to dryness. The residue was dissolved in HCl/MeOH (1N, 10 ml), and the solvent was evaporated to give a white solid. This white solid was stirred in ethyl ether (10 ml) and VE-ONH2-1 (960 mg, 66% yield) was obtained after filtration and drying. The compound was characterized by NMR and MS as follows: 1) C-NMR (CDCl$_3$): 11.71, 12.2, 12.66, 21.04, 24.49, 32.45, 37.97, 72.48, 73.82, 117.48, 119.20, 121.78, 122.98, 145.17, 145.57 ppm; 2) H-NMR (CDCl$_3$): 1.27 (s, 3H), 1.82 (m, 3H), 1.93 (m, 1H), 2.10 (s, 6H), 2.15 (s, 3H), 2.16 (t, 2H), 3.87 (m, 2H), 4.93 (b, 2 NH, 1 OH) ppm; and 3) MS (ESI): 266.2 [M+H]$^+$.

Synthesis of 2-(6-Methoxymethoxy-2,5,7,8-tetramethylchroman-2-yl)ethanol (compound 3): 2-(6-Hydroxy-2,5,7,8-tetramethylchroman-2-yl)ethanol (compound 1) (13.95 g, 55.7 mmol) was dissolved in DMF (125 mL) and cooled in an ice-bath with a constant argon-purge, as shown in FIG. 5. Sodium hydride (2.27 g, 94.6 mmol) was added to the solution, and it was removed from the ice-bath and stirred at RT for 45 minutes. The solution was re-cooled in an ice-bath, and chloromethyl methyl ether (4.23 mL, 55.7 mmol) was added to it. The reaction solution was removed from the ice-bath, and was stirred at room temperature.

TLC (silica gel 60 F$_{254}$ plates; hexane:ethyl acetate (1:1)) indicated the reaction to be complete after 3 hours, and therefore, it was worked-up as follows. The reaction solution was poured into 2.0 L of water, and this was extracted with 1.0 L of chloroform. The aqueous layer was left overnight which allowed more residual organic material to separate from it, as shown in FIG. 5. This organic layer was separated from the aqueous layer, and was combined with the original organic fraction. The aqueous layer was extracted once more with 1.0 L of chloroform. Each of the two organic fractions were back-extracted with 250 mL of water. The organic fractions were combined and concentrated to an oil which weighed 12.52 g. The compound was characterized by NMR and MS as follows: 1) C-NMR (CDCl$_3$): 12.49, 12.83, 13.75, 20.90, 23.68, 32.11, 42.44, 57.93, 59.53, 75.79, 99.93, 117.77, 123.09, 126.81, 128.66, 147.67, 147.75 ppm; 2) H-NMR (CDCl$_3$): 1.28 (s, 3H), 1.78 (m, 1H), 1.91 (m, 3H), 2.07 (s, 3H), 2.15 (s, 3H), 2.19 (s, 3H), 2.37 (s, 1 OH), 2.63 (t, 2H), 3.61 (s, 3H), 3,90 (m, 2H), 4.85 (s, 2H) ppm; and 3) MS (ESI): 317.2 [M+Na]$^+$, 611.5 [2M+Na]$^+$.

Synthesis of 2-(6-Methoxymethoxy-2,5,7,8-tetramethylchroman-2-yl)ethyl p-toluenesulfonate (compound 4): 2-(6-methoxymethoxy-2,5,7,8-tetramethylchroman-2-yl)ethanol (compound 3) (15.10 g, 51.3 mmol) was diluted in 60 mL of chloroform, and triethylamine (14.3 mL, 103 mmol) was added to it. The solution was cooled in an ice-bath with stirring. p-Toluenesulfonyl chloride (11.75 g, 61.6 mmol) was added to the solution, and the reaction solution was removed from the ice-bath, and was stirred at room temperature (RT).

TLC (silica gel 60 F$_{254}$ plates; hexane:ethyl acetate (2:1)) indicated the reaction to be complete after 3 hours, and therefore, it was worked-up as follows. The reaction solution was concentrated to a paste. The paste product was taken-up in 75 mL of ethyl acetate, and 150 mL of hexane was slowly added with stirring. The salt by-product precipitated out of solution, and was removed by filtration. The filter cake was rinsed with a small amount of ethyl acetate. The filtrate was concentrated to a dark oil which weighed 24.69 g. The oil was diluted with 30 mL hexane:ethyl acetate (5:1), and was decanted onto a silica gel (230-400 mesh, 60 Å) flash column bed which measured ~5 cm×30 cm. The flash column was eluted with a mobile phase of hexane:ethyl acetate (5:1), and 24×~125 mL size fractions were collected. Based upon the TLC results of each fraction, appropriate fractions were combined and concentrated to a clear oil which weighed 16.15 g. The compound was characterized by NMR and MS as follows: 1) C-NMR (CDCl$_3$): 12.12, 12.81, 13.69, 20.76, 22.00, 24.36, 32.08, 38.64, 57.92, 67.30, 73.53, 99.93, 117.41, 123.28, 126.66, 128.25, 128.66, 130.19, 133.42, 145.11, 147.60 ppm; 2) H-NMR (CDCl$_3$): 1.21 (s, 3H), 1.76 (t, 2H), 1.92-1.96 (m, 2H), 1.94 (s, 3H), 2.12 (s, 3H), 2.16 (s, 3H), 2.43 (s, 3H), 2.54 (t, 2H), 3.60 (s, 3H), 4.21 (m, 1H), 4.28 (m, 1H), 4.84 (s, 2H), 7.32 (d, 2H), 7.75 (d, 2H) ppm; and 3) MS (ESI): 417.3 [M+Na]$^+$, 919.5 [2M+Na]$^+$.

Synthesis of N-[2-(6-Methoxymethoxy-2,5,7,8-tetramethylchroman-2-yl)ethyl]piperazine (compound 5): 2-(6-Methoxymetoxy-2,5,7,8-tetramethylchroman-2-yl)ethyl p-toluenesulfonate (compound 4) (16.01 g, 35.7 mmol) was diluted in 200 mL of toluene, and piperazine (6.15 g, 71.4 mmol) was added to it, as shown in FIG. 5. The reaction solution was heated at reflux. TLC (silica gel 60 F$_{254}$ plates; hexane:ethyl acetate (2:1) and chloroform:methanol (4:1)) indicated the reaction to be complete after 2.5 hours, and therefore, it was worked-up as follows: The reaction solution was cooled to room temperature (RT) which caused residual piperazine to precipitate out, and the piperazine was removed by filtration. The filter cake was rinsed with toluene, and this rinsing was combined with the filtrate. The filtrate was concentrated to an oil which weighed 15.79 g. The oil was diluted with chloroform (25 mL), and it was decanted onto a silica gel column (230-400 mesh, 60 Å) that had been prepared with chloroform:methanol (6:1) slurry. The flash column bed measured ~5 cm×30 cm. The flash column was eluted with the following mobile phase systems: 1) CHCl$_3$:MeOH (6:1); 3 L; -collected 40×~30 mL fractions, followed by 8×~100 mL fractions; 2) CHCl$_3$:MeOH (2:1); 1.8 L; -collected 4×200 mL fractions, followed by 2×400 mL fractions; and 3) CHCl$_3$:MeOH (1:1); 0.8 L; -collected 2×400 mL fractions. Based upon the TLC results of each fraction, appropriate fractions were combined and concentrated to a clear oil which weighed 10.70 g. The compound was characterized by NMR and MS as follows: 1) C-NMR (CDCl$_3$): 12.25, 12.80, 13.68, 20.99, 24.42, 32.07, 36.59, 46.48, 54.42, 55.19, 57.88, 74.35, 99.89, 117.69, 123.28, 126,51, 128.45, 147.25, 148.16 ppm; 2) H-NMR (CDCl$_3$): 1.23 (s, 3H), 1.78 (m, 5H), 2.05 (s, 3H), 2.12 (s, 3H), 2.16 (s, 3H), 2.39 (b, 4H), 2.48 (t, 2H), 2.57 (t, 2H), 286 (t, 4H), 3.59 (s, 3H), 4.82 (s, 2H) ppm; and 3) MS (ESI): 363.3 [M+H]$^+$.

Synthesis of tert-Butyl phthalimidooxyacetate (compound 6): N-hydroxyphthalimide (3.87 g, 23 mmol) and potassium carbonate (2.14 g, 15.5 mmol) were suspended in 1-methyl-2-pyrrolidinone (23 mL) and heated to 40° C. t-Butyl-bromoacetate (4.58 g, 23 mmol) was added, and the reaction temperature was increased to 50° C., and held at this temperature for 4 hours, and then poured into 50 mL of ice water to precipitate the product. The solid was collected on a glass filter funnel and washed with water until the filtrate was colorless. The precipitate was dried on the filter funnel with the house vacuum, and by azeotroping with chloroform. This afforded 5.92 g (91% yield) of product with a melting point of 143-144° C. The compound was characterized as NMR and MS as follows: 1) C-NMR (CDCl$_3$): 28.39, 73.82, 83.38, 124.04, 129.22, 134.99, 163.40, 166.29 ppm; 2) H-NMR (CDCl$_3$): 1.46 (s, 9H); 4.68 (s, 2H); 7.74 (m, 2H); 7.83 (m, 2H) ppm; and 3) MS (ESI): 300.2 [M+Na]$^+$, 577.3 [2M+Na]$^+$.

Synthesis of Phthalimidooxyacetic Acid (Compound 7): tert-Butyl phthalimidooxyacetate (compound 8) (0.5 g, 1.8 mmol) was dissolved in dichloromethane (5 mL), and trifluoroacetic acid (1.5 mL) was added, as illustrated in FIG. 6. The mixture was stirred at RT for one hour and evaporated to dryness. The residue was azeotroped with chloroform (3 times) to yield a white solid weighing 0.393 g (100% yield). The compound was characterized by NMR and MS as follows: 1) C-NMR (d-DMSO): 73.73, 124.13, 129.43, 135.65, 163.46, 168.87 ppm; and 2) H-NMR (d-DMSO): 4.76 (s, 2H); 7.86 (s, 4H) ppm; and 3) MS (ESI): 220.0 [M–H]$^-$, 463.1 [2M-2H+Na]$^-$.

Synthesis of N-[2-(6-Methoxymethoxy-2,5,7,8-tetramethylchroman-2-yl)ethyl]-N'-(pthalimidooxyacetyl)-piperazine (compound 8): To a solution of chroman (compound 5) (5.0 g, 13.8 mmole) in dichloromethane (30 ml), compound 7 (3.5 g, 16 mmole) and N-hydroxysuccinimide (1.8 g, 16 mmole) were added, as shown in FIG. 7. The mixture was stirred at room temperature until the formation of a clear solution and then 1,3-dicyclohexylcarbodiimide (16 ml, 1.0 N in dichloromethane, 16.0 mmole) was added. The mixture was stirred at room temperature overnight. The white solid was removed by filtration, and the solvent was evaporated under reduced pressure. The residue was dissolved in chloroform (100 ml), and the solution was washed by saturated NaHCO$_3$ (100 ml) and H$_2$O (100 ml). The organic solvent was evaporated to dryness to give a yellow glass. This yellow glass was passed through a silica column with MeOH/EtOAc (5/95) to give a yellow glass as product 8 (5.5 g, 70% yield). The compound was characterized as NMR and MS as follows: 1) C-NMR (CDCl$_3$): 11.983, 12.861, 13.729, 20.117, 23.550, 30.055, 35.951, 41.494, 45.291, 52.196, 52.087, 57.051, 73.411, 75.309, 99.049, 116.801, 122.420, 123.437, 125.719, 127.671, 128.283, 134.187, 146.465, 147.220, 162.451, 163.470 ppm; 2) H-NMR (CDCl$_3$): 1.244 (s, 3H), 1.790 (m, 4H), 2.052 (s, 3H), 2.119 (s, 3H), 2.157 (s, 3H), 2.9-2.6 (m, 8H), 3.586 (s, 3H), 3.62 (b, 2H), 3.72 (b, 2H), 4.813 (s, 2H), 4.825 (s, 2H), 7.726 (m, 2H), 7.803 (m, 2H) ppm; and 3) MS (ESI): 566.4 [M+H]$^+$, 588.4 [M+Na]$^+$.

Synthesis of N-[2-(6-Methoxmethoxy-2,5,7,8-tetramethylchroman-2-yl)ethyl]-N'-(aminooxyacetyl)-piperazine (compound 9): Compound 8 (2.0 g, 3.6 mmole) was dissolved in ethanol (50 ml) and hydrazine (4.0 g, 250 mmole) was added, as illustrated in FIG. 7. The mixture was stirred at room temperature overnight, and the white solid was removed by filtration. The filtrate was evaporated to dryness and the residue was dissolved in methanol (250 ml). The solvent was evaporated to give a white solid. The residue was dissolved in HCl/MeOH (1N, 10.0 ml) and the solvent was evaporated to give a white solid. This white solid was suspended in Methanol-ethyl ether (25 ml, 4/1) and compound 9 (1.89 g, 95% yield) was obtained after filtration and drying. The compound was characterized by NMR as follows: 1) C-NMR (CD$_3$CO$_2$D: 12.150, 12.700, 13.579, 21.086, 23.717, 32.112, 33.863, 40.137, 42.607, 52.078, 54.014, 57.684, 72.200, 74.278, 100.292, 118.375, 127.367, 129.194, 148.197, 148.478, 168.923, 178.352 ppm; and 2) H-NMR (CD$_3$CO$_2$D): 1.283 (3H), 1.86 (m, 2H), 2.062 (s, 3H), 2.128 (s, 3H), 2.158 (s, 3H), 2.17-2.27 (m, 2H), 2.641 (m, 2H), 3.15 (b, 1H), 3.351, 3.478 (m, 4H), 3.599 (s, 3H), 3.851 (m, 4H), 1.65 (b, 1H), 4.877 (s, 2H), 4.887 (s, 1H), 5.10 (b, 1H) ppm.

Synthesis of N-[2-(6-Hydroxy-2,5,7,8-tetramethylchroman-2-yl)ethyl]-N'-(amiooxyacetyl)-piperazine (VE-ONH2-2): Compound 9 (1.8 g, 3.4 mmole) was suspended in acetic acid/water (20 ml, 4/1), and TFA (10 ml) was added as further illustrated in FIG. 7. The solution was stirred at room temperature until TLC (MeOH/CHCl$_3$, 10/90) showed the completion of the reaction. The solvents were evaporated to dryness. The residue was dissolved in methanol (30 ml) and the solvent was evaporated to give a white solid. The residue was dissolved in a mixture of HCl/MeOH (0.5N, 40 ml) and the solvent was evaporated to dryness to give a yellow solid. The product VE-ONH2-2 (1.5 g, 86%) was obtained as light white powder after treatment with ethyl ether (100 ml). The compound was characterized by NMR and MS as follows: 1) BC-NMR (D$_2$O): 11.41, 11.54, 12.36, 20.25, 22.94, 31.70, 32.25, 39.26, 41.19, 41.66, 41.85, 41.96, 51.36, 51.49, 51.69, 53.24, 53.64, 70.70, 70.96, 73.27, 74.16, 74.23, 118.83, 122.40, 123.02, 124.45, 144.80, 144.89, 167.50, 170.03, 170.21 ppm; 2) H-NMR (D$_2$O): 1.19 (s, 3H), 1.76 (b, 2H), 1.9-2.1 (m, 2H), 2.0 (s 3H), 2.02 (s, 3H), 2.04 (s, 3H), 2.54 (b, 2H), 2.307 (m, 4H), 3.53 (m, 4H), 3.75 (m, 1H), 4.01 (m, 1H), 4.49 (m, 1H), 4.71 (m, 1H), 6.62*, 6.64* (d, 0.3H), 7.15*, 7.16* (d, 0.3H) ppm. (*Formaldehyde adduct peaks); and 3) MS (ESI): 392.2 [M+H]$^+$ (VE-ONH2-2), 403.3 [M+H]$^+$ (Formaldehyde adduct of VE-ONH2-2).

Synthesis of N-[2-(6-Methoxymethoxy-tetramethylchroman-2-yl)ethyl]-N'-(N-tert-butyloxycarbonyl-S-trityl-cysteinyl)-(compound 10): To a solution of chroman (compound 5) (4.0 g, 11 mmole) in dichloromethane (30 ml), N-Boc-S-trityl-cysteine (5.7 g, 12.4 mmole) and 1-hydroxybenzotriazole hydrate (540 mg, 4.0 mmole) were added, as shown in FIG. 8. The mixture was stirred at room temperature until the formation of a clear solution, and then 1,3-dicyclohexylcarbodiimide (13 ml, 1.0 N in dichloromethane, 13.0 mmole) was added. The mixture was stirred at room temperature overnight. At the completion of the reaction, the white solid was removed by filtration and the solvent was removed under evaporation. The residue was dissolved in chloroform (20 ml), and this solution was passed through a silica column with solvents of hexane and ethyl acetate (1/1) and ethyl acetate to give a white glass as product (compound 10) (7.6 g, 81% yield). The compound was characterized as NMR and MS as follows: 1) C-NMR (CDCl3): 12.31, 12.85, 13.74, 20.90, 24.229, 28.720, 31.973, 35.297, 36.197, 36.254, 41.97, 45.22, 49.48, 49.66, 52.98, 53.48, 53.54, 57.92, 67.23, 74.05, 80.22, 99.93, 117.56, 119.50, 123.22, 124.53, 127.18, 128.36, 129.97, 144.86, 147.46, 147.92, 155.37, 169.29 ppm; 2) H-NMR (CDCl$_3$): 1.21 (s, 3H), 1.42 (s, 9H), 1.718 (m, 5H), 2.05 (s, 3H), 2.13 (s, 3H), 2.18 (s, 3H), 2.38 (m, 3H), 2.45 (m, 3H), 2.57 (m, 4H), 3.18 (b, 1H), 3.28 (b, 1H), 3.56 (b, 1H), 3.60 (s, 3H), 3.65 (b, 1H), 4.44

(b, 1H), 4.84 (s, 2H), 5.27 (d, 1H) ppm; and 3) MS (ESI): 808.5 [M+H]$^+$, 830.5 [M+Na]$^+$.

Treatment of compound 10 with 1 N HCl: Compound 10 (3.0 g, 3.7 mmole) was dissolved in MeOH/HCl (1N, 70 ml) and the mixture was stirred at room temperature. A white solid was formed after 10 minutes of stirring. The mixture was further stirred at room temperature for 3 hours, methanol (200 mL) was added, and stirring was continued overnight. The solvents were evaporated to dryness, and the residue was dissolved in methanol (200 ml). The solvent was evaporated to dryness to give a white glass containing compound 12a as the major product and compound 12b as the minor product, as indicated by TLC. This mixture (2.9 g) was used for next step without further purification, as shown in FIG. 8.

Synthesis of N-[2-(6-Hydroxy-tetramethylchroman-2-yl) ethyl]-N'-(cysteinyl)-piperazine (VE-CYS-1): To a solution of product mixture of compounds 12a and 12b (2.9 g, 3.4 mmole) in dichloromethane (20 ml), trifluoroacetic acid (3 ml) was added, as illustrated in FIG. 8. The solution turned yellow. The mixture was stirred at room temperature for 5 minutes. Triethylsilane (1 ml) was added to the solution, and the mixture was stirred for 30 minutes. The solvent was evaporated to dryness, and was co-evaporated with dichloromethane (20 ml). The residue was dissolved in DI water (50 ml) and extracted with dichloromethane (50 mL) to remove the trityl by-product. The aqueous layer was evaporated, and the residue was dissolved in HCl/MeOH (1N, 10 ml). The solvent was evaporated to dryness to give a white glass. This white glass was dissolved in methanol (8 ml). The solution was poured into ethyl ether with stirring. After stirring at room temperature for 30 minutes, and the mixture was filtered to give a white solid. This solid was dried at high vacuum to give product VE-CYS-1 (1.45 g, 78% yield). The compound was characterized by NMR and MS as follows: 1) C-NMR (D$_2$O): 11.278, 11.430, 12.237, 20.152, 22.855, 24.255, 24.764, 31.639, 32.058, 39.772, 42.878, 51.169, 51.472, 52.025, 52.229, 53.104, 53.245, 74.184, 118.814, 122.450, 122.961, 124.489, 144.681, 144.813, 166.715, 167.182 ppm; 2) H-NMR (D$_2$O): 1.310 (s, 3H), 1.879 (m, 2H), 2.02-2.17 (m, 2H), 2.097 (s, 6H), 2.151 (s, 3H), 2.665 (t, 2H), 3.301 (dd, 1H), 3.111 (dd, 1H), 3.24 (b, 3H), 3.337 (m, 1H), 3.556 (m, 1H), 3.6-3.72 (m, 3H), 4.221 (b, 1H), 4.4.5-4.8 (m, 2H) ppm, and 3) MS: (ES+) MS: 422.5 [M+H]$^+$.

Treatment of 10 with TFA/Triethylsilane: Compound 10 (50 mg) was added to trifluoroacetic acid (0.3 ml), as shown in FIG. 8. The solution turned to yellow. The mixture was stirred at room temperature for 5 minutes. Triethylsilane (0.1 ml) was added to the solution, and the mixture was stirred for 30 minutes. The solvent was evaporated to dryness to give a white precipitate which was analyzed by mass spectrometry. The MS results indicated that compound 11 was obtained as the major product and the VE-CYS-1 as a minor product. The compound was characterized by MS as follows: MS (ESI): 422.3 [M+H]$^+$ (VE-CYS-1), 434.2 [M+H]$^+$ (11).

Synthesis of N-[2-(6-Methoxymethoxy-tetramethylchroman-2-yl)ethyl]-N'-(N-tert-butyloxycarbonyl-S-trityl-penicillamyl-piperazine (compound 13): To a solution of chroman (compound 5) (5.0 g, 13.2 mmole) in dichloromethane (60 mL), Boc-S-trityl-penicillamine (7.3 g, 15.0 mmole), and 1-hydroxybenzotriazole hydrate (540 mg, 4.8 mmole) were added. The mixture was stirred at room temperature until the formation of a clear solution and then 1,3-dicyclohexylcarbodiimide (15 mL, 1.0 N in dichloromethane, 15.0 mmole) was added. The mixture was stirred at room temperature overnight. At the end of the reaction, the white solid was removed by filtration and the solvent was removed under evaporation. The residue was dissolved in chloroform (20 mL) and this solution was passed through a silica column with solvents of hexane and ethyl acetate (1:1) and ethyl acetate to give a white glass as product (compound 13) (7.5 g, 80% yield). This compound was characterized by NMR and MS as follows: 1) $^{13}$C-NMR (CDCl$_3$): 12.10, 12.64, 13.53, 20.77, 24.17, 25.06, 25.81, 27.11, 28.54, 31.84, 34.15, 36,73, 42.17, 46.90, 53.18, 53.45, 53.56, 55.13, 56.14, 57.72, 68.46, 74.05, 79.88, 99.71, 117.42, 123.07, 126.39, 126.69, 127.79, 128.35, 130.40, 145.13, 147.14, 147.87, 155.48, 169.15 ppm. 2) $^1$H-NMR (CDCl$_3$): 0.96 (s, 3H), 0.98 (s, 3H), 1.27 (s, 3H), 1.45 (s, 9H), 1.83 (m, 4H), 2.08 (s, 3H), 2.16 (s, 3H), 2.20 (s, 3H), 2.44 (b, 4H), 2.54 (b, 2H), 2.16 (t, 2H), 3.54 (b, 2H), 3.63 (s, 3H), 3.66 (b, 2H), 4.57 (b, 1H) 4.87 (s, 2H), 5.495 (d, 1H), 7.19 (t, 3H), 7.27 (t, 6H), 7.595 (d, 6H) ppm, and 3) MS (ESI): 836.6 [M+H]$^+$; 858.6 [M+Na]$^+$.

Treatment of compound 13 with 1 N HCl: Compound 13 (6.5 g, 7.2 mmole) was dissolved in MeOH/HCl (1N, 120 mL) and was stirred at room temperature. A white solid was formed after 10 minutes. The mixture was stirred at room temperature overnight. The solvents were evaporated to dryness and the residue was dissolved in a mixture of methanol (200 mL). The solvent was evaporated to dryness to give a white glass containing compound 14a (major product) and compound 14b (minor product) as indicated by TLC. This mixture (6.1 g) was used for next step without purification.

N-[2-(6-Hydroxy-tetramethylchroman-2-yl)ethyl]-N'-(penicillamyl)-piperazine (VE-PEN-1): To a solution of compounds 14a and 14b (6.1 g, 6.8 mmole) in chloroform (100 ml), trifluoroacetic acid (15 mL) was added. The solution was turned to yellow color. The mixture was stirred at room temperature for 5 minutes. Triethylsilane (3 mL) was added to the solution and the mixture was stirred for 60 minutes. The solvent was evaporated to dryness and was co-evaporated with chloroform (100 mL). Residue was dissolved in methanol-HCl (1N, 120 mL). The solvent was evaporated to dryness to give a white solid. This white glass was dissolved in methanol (20 mL). The solution was poured into ethyl ether (50 mL) with stirring. The mixture was stirring at room temperature for 30 minutes and was filtered to give a white solid. This solid was dried at high vacuum to give product VE-PEN-1 (3.0 g, 80% yield). 1.0 g of VE-PEN-1 was dissolved in DI water (100 mL) and NaOH (0.1N) was used to adjust the pH of the solution to 6.5. Lyophilization of the solution gave 0.65 g white glass as the final product. The compound was characterized by NMR and MS as follows: 1) $^{13}$C-NMR (D$_2$O): 11.46, 11.62, 12.42, 20.38, 23.17, 23.22, 28.42, 29.00, 31.92, 32.44, 40.42, 44.68, 45.50, 51.60, 51.69, 51.77, 53.05, 53.13, 57.95, 74.58, 119.12, 122.64, 123.14, 124.65, 144.93, 144.97, 168.11 ppm. 2) $^1$H-NMR (D$_2$O): 1.29 (s, 3H), 1.46 (s, 3H), 1.51 (s, 3H), 1.89 (m, 2H), 2.00 (m, 2H), 2.09 (s, 3H), 2.10 (s, 3H), 2.14 (s, 3H), 2.66 (t, 2H), 3.05-3.4 (m, 6H), 3.7-4.1 (m, 4H), 4.49 (s, 1H) ppm, and 3) MS (ESI): 450.3 [M+H]$^+$

ANTIOXIDANT AND CARBONYL TRAPPING PROPERTIES

Tests were conducted to evaluate the antioxidant and carbonyl trapping properties of therapeutic compositions according to various embodiments of the present invention.

A Trolox equivalent antioxidant activity (TEAC) test was conducted to assess the antioxidant properties as described below in greater detail.

TEAC Assay

The TEAC antioxidant activity was measured by the ABTS [2,2'-Azinobis-(3-ethylbenzothiazoline-6-sulphonic acid)] decolorization assay. In this method, a stable radical (ABTS radical cation) is formed, and the adsorption maxima is determined. See, for example, R. Ree, N. Pellegrini, A. Proteggente, A. Pannala, M. Yang and C. Rice-Evans, Antioxidant activity applying an improved ABTS radical cation decolorization assay, *Free Rad. Biol. & Med.*, 26 (9/10), 1231-1237 (1999). The addition of antioxidant to the preformed radical cation reduces it to an extent and on a time-scale depending on the antioxidant activity, the concentration of the antioxidant and the duration of the reaction. Thus, the extent of reduction (decolorization) as percentage inhibition of the ABTS radical cation is determined as a function of concentration and time and calculated relative to the reactivity of Trolox as a standard under the same conditions. The antioxidant capacity of the target vitamin E derivatives is summarized in Table 1, as shown below. The TEAC value is calculated by the ratio of % of Inhibition of antioxidant compound/% Inhibition of Trolox.

TABLE 1

TEAC Values

| Compound | TEAC (Slope) | TEAC (Ratio % Inhibition) |
| --- | --- | --- |
| VE-ONH2-1 | $0.9_{(r^2 = 0.9948)}$ | 0.9-1.0 |
| VE-ONH2-1 | $0.8_{(r^2 = 0.9997)}$ | 0.5-0.8 |
| VE-CYS-1 | $1.4_{(r^2 = 0.9997)}$ | 1.4-1.5 |
| VE-PEN-1 | $1.3_{(r^2 = 0.9996)}$ | 1.6-2.1 |

CARBONYL TRAPPING ANALYSIS

In general, the carbonyl trapping reagent, at different concentrations, was allowed to react with the carbonyl compounds in thermally degraded peritoneal dialysis solution (PD-2) at room temperature. See, for example, C. B. Nilsson-Thorell, N. Muscalu, A. H. G. Andren, P. T. T. Kjellstrand, and A. P. Wieslander and T. Miyata and K. Isehara-Shi. Drugs for relieving carbonyl stress and peritoneal dialysates. European Patent No. 1108343, (2000) Heat sterilization of fluids for peritoneal dialysis gives rise to aldehydes. *Peritoneal Dialysis International*, 13, 208-213, (1993). D. M. Smith, T. E. Kleindienst and E. E. Hudgens. High performance liquid chromatographic method for an artifact-free measurement of aldehydes in the presence of ozone using 2,4-dinitrophenylhydrazine was conducted. See, *J. Chromatogr.*, 483, 431-436 (1989).

Following the carbonyl trapping reaction, the solution was treated with 2,4-dinitrophenylhydrazine to convert the residual carbonyl compounds to hydrazones. An internal standard that included the 2,4-dinitrophenylhydrazone of cyclohexanone was added, and the hydrazones were isolated by solid phase extraction. The extract was analyzed by electrospray LC/UV/MS. A low hydrazone response was indicative of an effective trapping reagent. The responses from the test articles, reacted with various concentrations of trapping reagent, were compared to a control that was not treated with the trapping reagent. The control was a non-thermally degraded PD-2 solution.

Analytical test system (LC/UV/MS): The analytical test system was a Fisons Instruments VG Quattro Mass Spectrometer operating in the positive electrospray mode (ES+). The inlet was an HP 1090 Liquid Chromatograph equipped with an Adsorbosphere UHS $C_{18}$ 5µ column (Alltech lot number 105300), 150 mm×4.6 mm. The calibrant was Agilent Tuning Mix introduced by a Harvard syringe pump set at 5 µL/min.

The chromatography column flow rate was 1 mL/min. The effluent from the column was split between the UV detector and the mass spectrometer by means of 0.025-in (i.d.) PTFE tubing, approximately 1 m in length. This served as a restrictor, and the resulting flow to the mass spectrometer was approximately 0.1 mL/min. The mass spectrometer operating parameters are listed in Table 2 as shown below.

TABLE 2

Mass spectrometer operating parameters

| | |
| --- | --- |
| Solvent delay | 4.00 min |
| Full scan, range: | 200 to 600 da |
| Scan time | 2.50 sec |
| Inter Scan Time | 0.10 sec |
| Start time | 3.80 min |
| End time | 26.00 min |
| Cone voltage | 30 volts |
| Source Temperature | 140° C. |

The HPLC injection volume was 100 µL, and the solvent gradient occurred as described below in Table 3. Solvent A was water; solvent B was 0.1% trifluoroacetic acid (TFA) in acetonitrile; and solvent C was methanol.

TABLE 3

Solvent Gradient.

| Time | % A | % B | % C | Flow rate (mL/min) |
| --- | --- | --- | --- | --- |
| 0.00 | 40.0 | 20.0 | 40.0 | 1.00 |
| 10.00 | 25.0 | 5.0 | 70.0 | 1.00 |
| 20.00 | 15.0 | 5.0 | 80.0 | 1.00 |
| 26.00 | 15.0 | 5.0 | 80.0 | 1.00 |
| 27.00 | 40.0 | 20.0 | 40.0 | 1.00 |
| 37.00 | 40.0 | 20.0 | 40.0 | 1.00 |

Internal Standard: Cyclohexanone 2,4-Dinitrophenylhydrazone

Synthesis Procedure

Concentrated sulfuric acid (2 mL) and 0.4456 g of 2,4-dinitrophenylhydrazine (2,4-DNP) were combined in a 25-mL Erlenmeyer flask. Water was added (2 to 3 mL) dropwise with swirling until the 2,4-DNP dissolved. This was followed by 10 mL of 95% ethanol. This solution was added, dropwise with swirling, to a solution of cyclohexanone, 0.5725 g, dissolved in 20 mL of 95% ethanol. A precipitate formed within 5 minutes. The mixture was refrigerated overnight. The precipitate was filtered to yield a yellow-orange crystalline solid. The product was re-crystallized from approximately 30 mL of absolute ethanol to afford 0.4 g of cyclohexanone 2,4-dinitrophenylhydrazone as orange flakes. The yield was 95%.

Preparation of Standard Solution

The 2,4-dinitrophenylhydrazone (approximately 20 mg), above, was accurately weighed into a 50-mL volumetric flask and diluted to volume with 0.60 M HCl (ethanolic).

The mixture was sonicated until dissolution was complete, approximately 15 minutes. The concentration was approximately 400 ug/mL.

Carbonyl Trapping Reaction

Three aliquots of the sample were treated, each with a different concentration of the trapping reagent. The target concentrations were approximately 1.25 mM, 5 mM and 10 mM. A fourth aliquot was not treated with trapping reagent. The trapping reagent was accurately weighed into three separate tared VOA vials. The test solution was transferred to the vials by means of an Eppendorf pipet. The vials were swirled to dissolve the reagent and then left to stand at room temperature for 16 to 22 hours. They were then treated as described in below. Typical masses of trapping reagent and volumes of test solution were shown in Table 4 below for a candidate compound having a molar mass of 500 amu. Specific masses were calculated for individual compounds.

TABLE 4

Typical masses for a Candidate Trapping Reagent and Typical Volumes of Test Solutions

| Target Concentration | Amount of trapping reagent (assuming a MW of ~500 amu) | Volume of test solution |
|---|---|---|
| 0 mM | 0 | 4 mL |
| 1.25 mM | 10 mg | 16 mL |
| 5 mM | 10 mg | 4 mL |
| 10 mM | 20 mg | 4 mL |

2,4-Dinitrophenylhydrazine (2,4-DNP) Reagent 2,4-Dintrophenylhydrazine (approximately 0.034 g) was dissolved in 50 mL of 0.6 M HCl (ethanolic). The concentration of 2,4-DNP was approximately 2.4 mM (after accounting for 30% moisture in the commercially available material)

Hydrazone Formation From Residual Carbonyl Compounds in PD-2 Solutions:

Test solutions (thermally degraded PD-2 solution, either treated or not treated with the trapping reagent), control (non-degraded PD-2) and water (for a method blank) were treated as follows. A 2-mL aliquot was combined with a 2-mL portion of the 2,4-DNP reagent solution as described above in a screw-top vial. The solution was mixed by swirling and allowed to stand for 60 min at room temperature. Then, 100 uL of the cyclohexanone 2,4-dinitrophenylhydrazine internal standard solution as described above was added. The solution was mixed thoroughly and treated by solid phase extraction as described below. The volumes used in the hydrazone formation reaction are summarized below in Table 5.

TABLE 5

Volumes Used in the Hydrazone Formation Reaction

| Target Concentration | Amount of trapping reagent (assuming a MW of ~500 amu) | Volume of trapping reaction solution | Volume of 2,4-DNP reagent[a] | Volume of internal standard solution added to a 2 mL aliquot after derivatization |
|---|---|---|---|---|
| 0 mM | 0 | 2 mL | 2 mL | 100 uL |
| 1.25 mM | 10 mg | 2 mL | 2 mL | 100 uL |
| 5 mM | 10 mg | 2 mL | 2 mL | 100 uL |
| 10 mM | 20 mg | 2 mL | 2 mL | 100 uL |

TABLE 5-continued

Volumes Used in the Hydrazone Formation Reaction

| Target Concentration | Amount of trapping reagent (assuming a MW of ~500 amu) | Volume of trapping reaction solution | Volume of 2,4-DNP reagent[a] | Volume of internal standard solution added to a 2 mL aliquot after derivatization |
|---|---|---|---|---|

[a]This volume was added to a 2-mL aliquot of the trapping reaction after specified times. The hydrazone derivatization was allowed to proceed for 60 min at room temperature.

Solid Phase Extraction

A Baker $C_{18}$ solid-phase extraction column (500 mg, 6 mL, wide mouth) was cleaned by sequentially applying and removing 1 mL each of methylene chloride (pulled through until dry), methanol, 1% aqueous methanol and water. During cleaning with the last three solvents, the top of the column was left wet with a thin layer of the solvent. Next, a 2.00-mL aliquot of the derivatization reaction solution as described above is applied with an Eppendorf pipet, and the solution is pulled through the column by house vacuum, again leaving a thin layer of solution at the top of the column. The retained material was washed twice with 1 mL portions of water, and the column was finally left under house vacuum for approximately three to five minutes to dry. The column was then eluted with 1 mL of acetonitrile.

Quantitation and Results

Both UV and MS data were obtained in this study. During the course of the work it was found that the UV response was more sensitive, and hence, the UV data were used for quantitation. Single-wavelength UV chromatograms were obtained from the data at 365 nm, the λmax for cyclohexanone 2,4-dinitrophenylhydrazone determined in this study. Peaks were integrated, and ratios were obtained for the sum of all hydrazone peaks relative to the internal standard. The ratios were plotted versus the concentration of the trapping reagent.

Figure 10A:
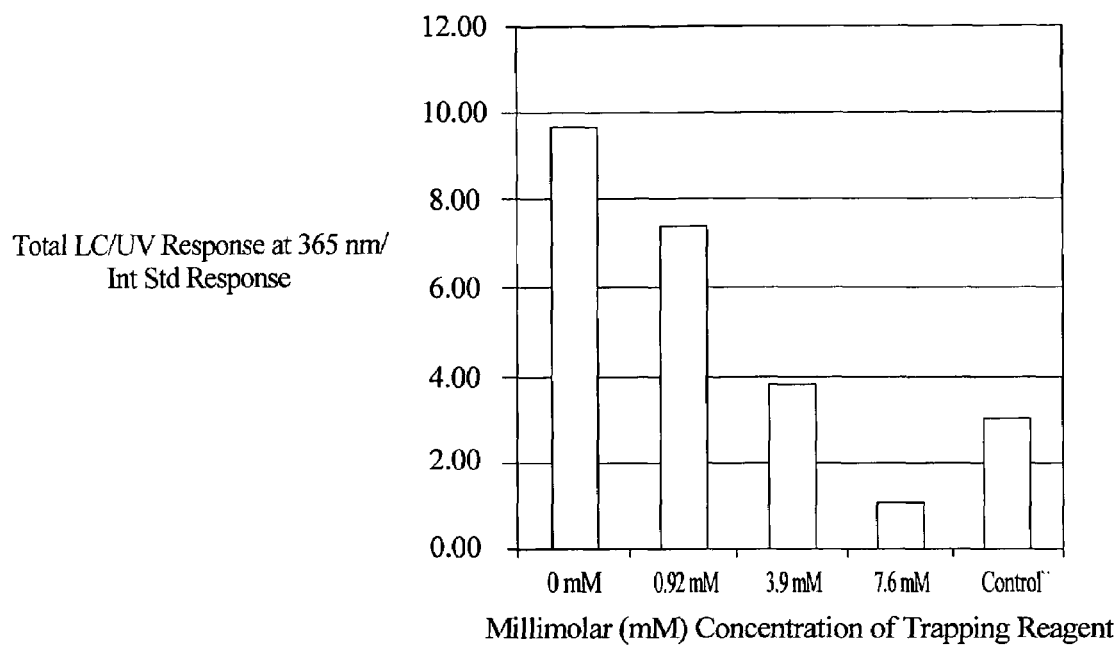
Figure 10B:
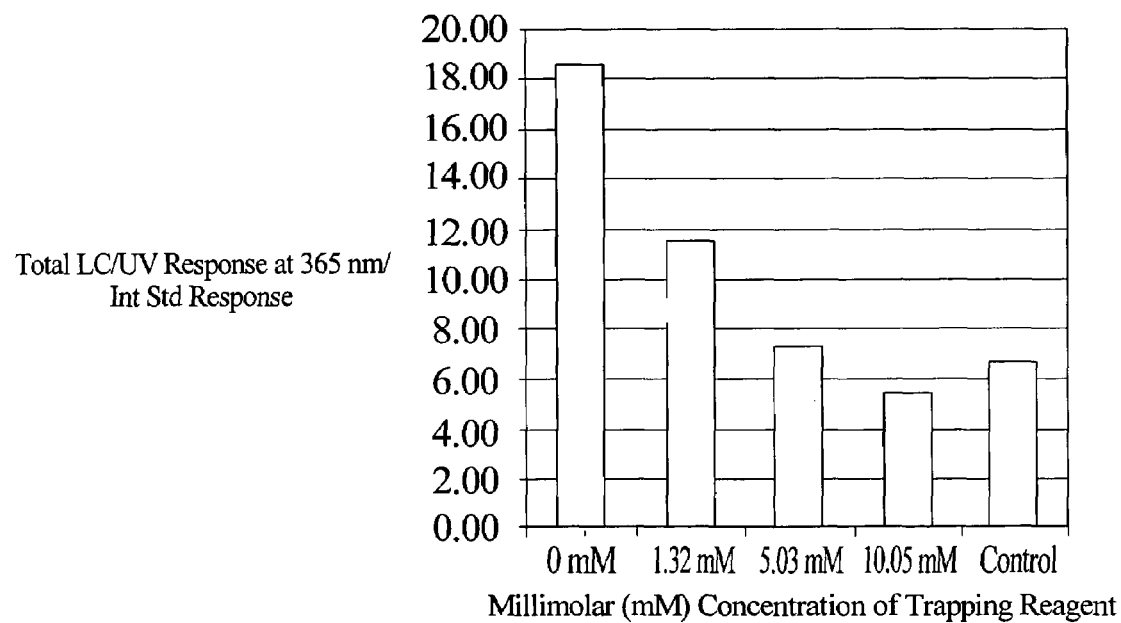

Certain early-eluting peaks were not included in the summation. These were attributed to the oxime or thiazolidine products from the reaction of the trapping reagent with carbonyl compounds. This was because the peaks were very early-eluting, indicative of high water solubility, and the peak areas increased with increasing concentration of trapping reagent. The results of the carbonyl trapping testing are illustrated in graphical form in FIG. 10A (VE-ONH2-1), FIG. 10B (VE-ONH2)-2, FIG. 10C (VE-CYS-1) and FIG. 10D (VE-PEN-1).

Aminoguanidine Test:

The carbonyl trapping properties of the Vitamin E derivatives of the present invention were further evaluated as compared to a known carbonyl trapping standard composition, namely, aminoguanidine. The Vitamin E derivatives included VE-CYS-1 and VE-PEN-1 made pursuant to an embodiment of the present invention as previously discussed. The test was conducted pursuant to similar carbonyl trapping test procedures as discussed above. The test results are illustrated in graphical form in FIG. 10E.

Figure 10E:
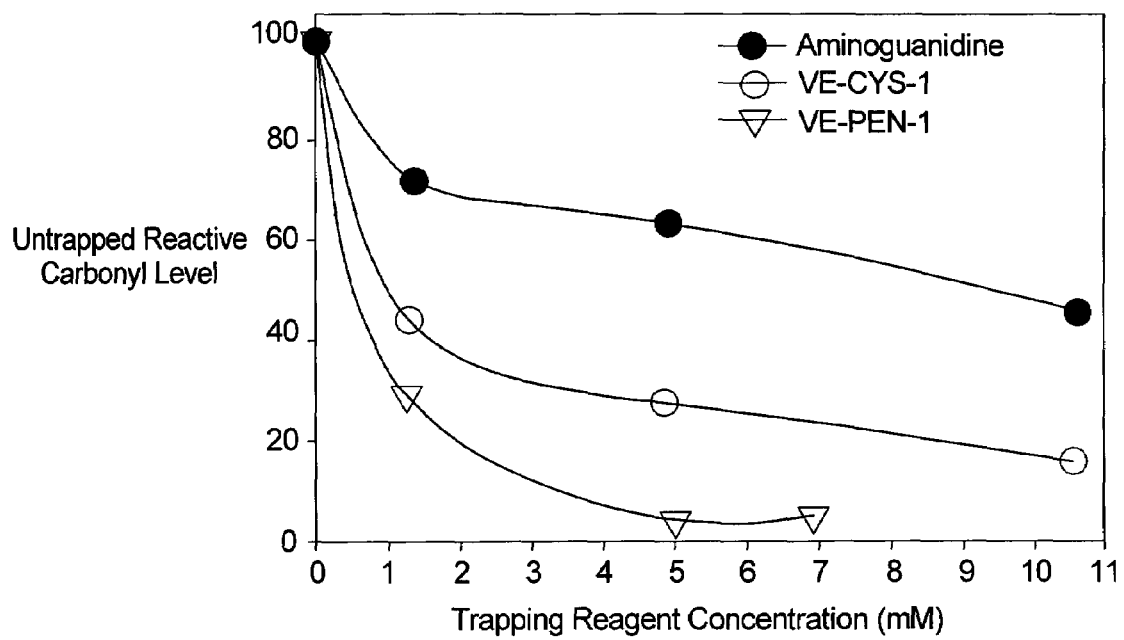

The antioxidant (TEAC Assay) and carbonyl trapping studies demonstrate that the Vitamin E derivatives made pursuant to an embodiment of the present invention display desirable and effective antioxidant and carbonyl trapping properties. As illustrated in Table 1, the vitamin E derivatives (e.g., VE-CYS-1 and VE-PEN-1) displayed enhanced antioxidant activity as compared to the Vitamin E standard compound (e.g., Trolox). Further, the Vitamin E derivatives displayed carbonyl trapping properties that generally increase in effect with increasing amounts as illustrated in FIGS. 10A-10D. The Vitamin E derivatives made pursuant to an embodiment of the present invention also displayed enhanced carbonyl trapping properties as compared to a known carbonyl trapping standard (e.g., aminoguanidine) as shown in FIG. 10E.

As previously discussed, the compositions of the present invention can be utilized in a variety of different applications. The compositions have both antioxidant and carbonyl trapping properties such that reactive oxygen species and reactive carbonyl species can be effectively inhibited. This can allow for effective reduction of inflammation and oxidative stress, such as in kidney disease patients. In this regard, cardiovascular and/or other associated disease can be effectively prevented and/or treated with the compositions of the present invention, particularly as applied during dialysis therapy.

It should be appreciated that the present invention can be used in a variety of different and suitable dialysis therapies to treat kidney failure. Dialysis therapy as the term or like terms are used throughout the text is meant to include and encompass any and all suitable forms of therapies that utilize the patient's blood to remove waste, toxins and excess water from the patient. Such therapies, such as hemodialysis, hemofiltration and hemodiafiltration, include both intermittent therapies and continuous therapies used for continuous renal replacement therapy (CRRT). The continuous therapies include, for example, slow continuous ultrafiltration (SCUF), continuous venovenous hemofiltration (CVVH), continuous venovenous hemodialysis (CVVHD), continuous venovenous hemodiafiltration (CVVHDF), continuous arteriovenous hemofiltration (CAVH), continuous arteriovenous hemodialysis (CAVHD), continuous arteriovenous hemodiafiltration (CAVHDF), continuous ultrafiltration periodic intermittent hemodialysis or the like. Preferably, the dialysis solutions are used during peritoneal dialysis, such as automated peritoneal dialysis, continuous ambulatory peritoneal dialysis, continuous flow peritoneal dialysis and the like. Further, although the present invention, in an embodiment, can be utilized in methods providing a dialysis therapy for patients having chronic kidney failure or disease, it should be appreciated that the present invention can be used for acute dialysis needs, for example, in an emergency room setting. Lastly, as one of skill in the art appreciates, the intermittent forms of therapy (i.e., hemofiltration, hemodialysis, peritoneal dialysis and hemodiafiltration) may be used in the in center, self/limited care as well as the home settings.

In an embodiment, the therapeutic compositions of the present invention are added to dialysis solutions, such as peritoneal dialysis solutions. The therapeutic compositions can be added to the dialysis solutions in any suitable and effective amount such that the compositions can effectively act to inhibit the activity of reactive oxygen species and reactive carbonyl species during dialysis therapy. This can prevent and/or treat disease, such as cardiovascular disease and the like, associated with kidney disease patients.

In general, the dialysis solution includes an osmotic agent, such as dextrose, glycerol, polyglucose, polypeptides, amino acids, glucose polymers and/or other suitable constituents in any suitable amount, such as from about 1.5% to about 4.25% by weight. The dialysis solution further includes one or more electrolytes, such as sodium, calcium, potassium, magnesium, chloride and/or the like in any suitable amount. The dialysis solution may also include other constituents, such as buffers including lactate, bicarbonate, and/or the like, and other constituents, such as stabilizers.

In an embodiment, the dialysis solution can be made from multiple solution components that can vary in the amounts and types of constituents thereof and have varying pH levels. A variety of different and suitable types of multi-part dialysis solutions can be utilized. For example, a multi-part bicarbonate-based solution can be found in U.S. Pat. No. 7,011,855, entitled BIOCHEMICALLY BALANCED PERITONEAL DIALYSIS SOLUTIONS, filed on Sep. 17, 2001, the disclosure of which is incorporated herein by reference. An example of a multi-part lactate-based solution can be found in U.S. Pat. No. 7,053,059, entitled DIALYSIS SOLUTIONS WITH REDUCED LEVELS OF GLUCOSE DEGRADATION PRODUCTS, filed on Jul. 25, 2003 the disclosure of which is herein incorporated by reference.

Another example of a bicarbonate-based solution can be found in U.S. Pat. No. 7,122,210, entitled BICARBONATE-BASED SOLUTIONS FOR DIALYSIS THERAPIES, filed on Jan. 11, 2002 and as further disclosed in U.S. Pat. No. 6,309,673, the disclosures of which are herein incorporated by reference. The bicarbonate-based solution can be made from solution components that have varying pH conditions, such as under moderate and extreme pH conditions. In an embodiment, the solution components can vary in pH from between about 1.0 to about 10.0. Once mixed, the desired pH of the mixed solution is maintained at a physiological acceptable level, such as between about 6.5 to about 7.6 (i.e., close to the pH of blood), prior to use.

For example, under moderate pH conditions, the bicarbonate-based solution can be formulated by the mixing of a bicarbonate concentrate with a pH that ranges from about 7.2 to about 7.9, preferably from about 7.4 to about 7.6, and a dextrose concentrate with a pH that ranges from about 3.0 to about 5.0. Under extreme pH conditions, for example, the bicarbonate concentrate has a pH that can range from about 8.6 to about 10.0 and is mixed with a dextrose concentrate that has a pH from about 1.0 to about 3.0, such as about 1.7 to about 2.2.

A variety of different and suitable acidic and/or basic agents can be utilized to adjust the pH of the bicarbonate concentrate, dextrose concentrate, and the like. For example, a variety of inorganic acids and bases can be utilized, such as hydrochloric acid, sulfuric acid, nitric acid, hydrogen bromide, hydrogen iodide, sodium hydroxide, the like or combinations thereof.

The solution components, such as a bicarbonate concentrate and a dextrose concentrate, can then be mixed in the solution bag and then administered as a mixed solution to the patient during peritoneal dialysis. An illustrative example of a multi-chamber container that separately contains solution components of a dialysis solution according to embodiment of the present invention is shown in FIG. 11.

It should be appreciated that the components of the dialysis solutions of the present invention can be housed or contained in any suitable manner such that the dialysis solutions can be effectively prepared and administered. In an embodiment, the present invention includes a multi-part dialysis solution in which two or more parts are formulated and stored separately, and then mixed just prior to use. A variety of containers can be used to house the various parts of the dialysis solution, such as separate containers (i.e., flasks or bags) that are connected by a suitable fluid communication mechanism.

The multi-chamber container or bag can be used to house the separate components of the solution including, for example, a dextrose concentrate and a buffer concentrate. In an embodiment, the separate components are mixed within the multi-chamber bag prior to use, such as applied during peritoneal dialysis.

Figure 11:
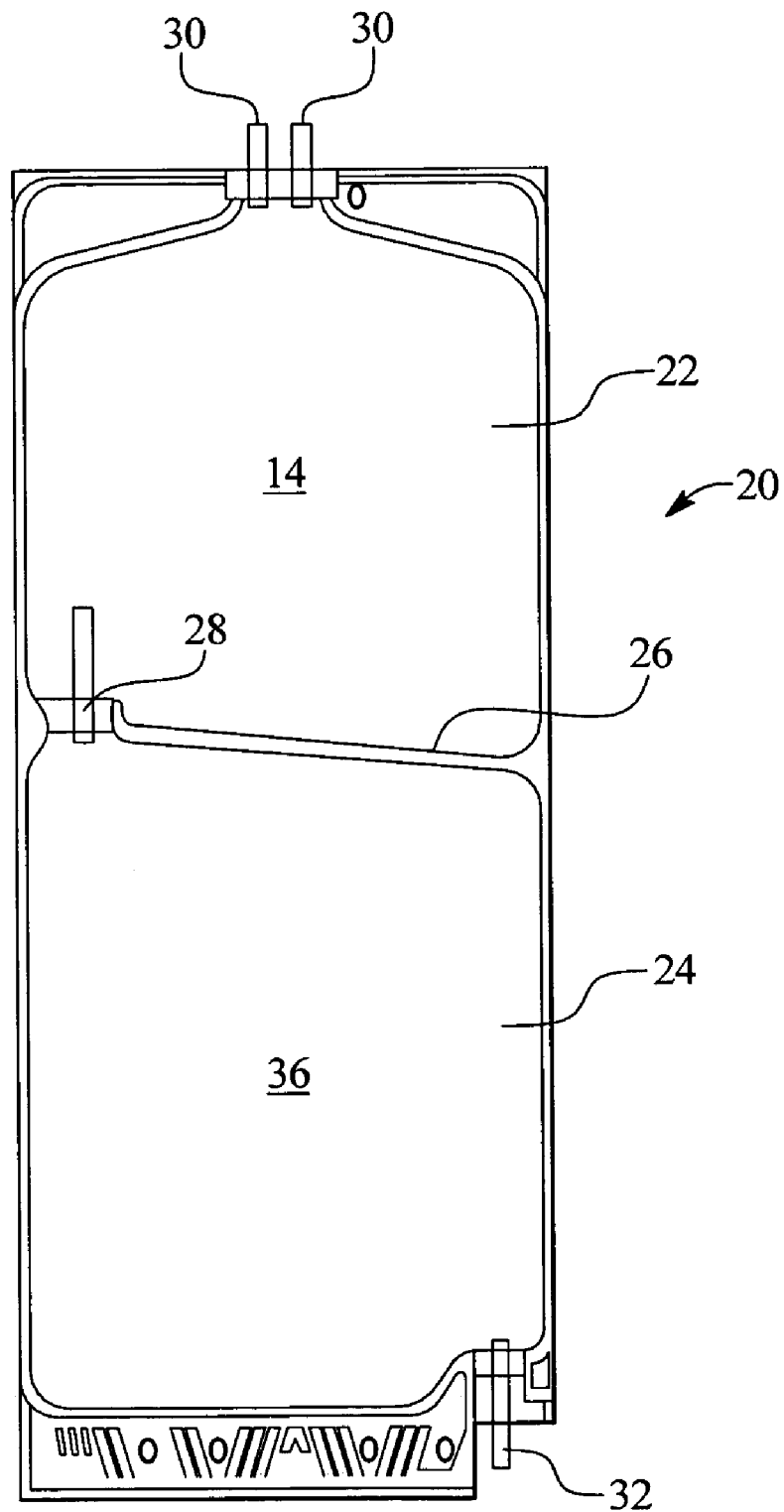
FIG. 11 illustrates a multiple chamber solution bag that contains a multi-part dialysis solution with a therapeutic composition according to an embodiment of the present invention.

FIG. 11 illustrates a suitable container for storing, formulating, mixing and administering a dialysis solution, such as during continuous ambulatory peritoneal dialysis, according to an embodiment of the present invention. The multi-chamber bag 20 has a first chamber 22 and a second chamber 24. The interior of the container is divided by a heat seal 26 into the two chambers. It should be appreciated that the container can be divided into separate chambers by any suitable seal.

Referring to FIG. 11, the multi-chamber container 20 has a frangible connector 28 to sealingly couple the first chamber 22 to the second chamber 24 instead of a peelable seal. To mix the solution within the multi-chamber bag 20, the frangible connector 28 is broken.

The first container or chamber 22 includes two port tubes 30 of suitable sizes and lengths. It should be appreciated that more or less than two port tubes may be used. One of the port tubes, for example, can be utilized to add other constituents to the first chamber 22 during formulation of the solution of the present invention, if necessary. The remaining port tube, for example, can be utilized to adaptively couple the first chamber 22 to the patient via a patient's administration line (not shown), be used to add additional other constituents or the like. The second container or chamber 24 has a single port tube 32 extending there from. In an embodiment, the port tube 32 is connected to a patient's administration line through which a solution can flow to the patient once the solution is mixed as described below.

In an embodiment, the transfer of product within the multi-chamber bag 20 can be initiated from the first chamber 22 to the second chamber 24 such that the components of each chamber can be properly mixed to form the dialysis solution of the present invention. In an embodiment, a dextrose concentrate 34 is contained in the first chamber 22 and a buffer concentrate 36 is contained in the second chamber 24. It should be appreciated that any suitable type or number of solution components can be separated with a multi-chamber bag and then mixed to form a mixed solution prior to administration to the patient. Illustrative examples of peritoneal dialysis solutions include those described in U.S. Pat. Nos. 7,011,855, 7,053,059 and 6,309,673 as discussed above.

The first chamber 22 is smaller in volume than the second chamber 24 such that the components of each chamber can be properly mixed once the transfer from the first chamber to the second chamber has occurred. Thus, the multi-chamber bag 20 can house at least two solution component parts that after mixture will result in a ready-to-use dialysis solution. An example of the multi-chamber container is set forth in U.S. Pat. No. 5,431,496, the disclosure of which is incorporated herein by reference. The multi-chamber bag can be made from a gas permeable material, such as polypropylene, polyvinyl chloride or the like.

Figure 12:
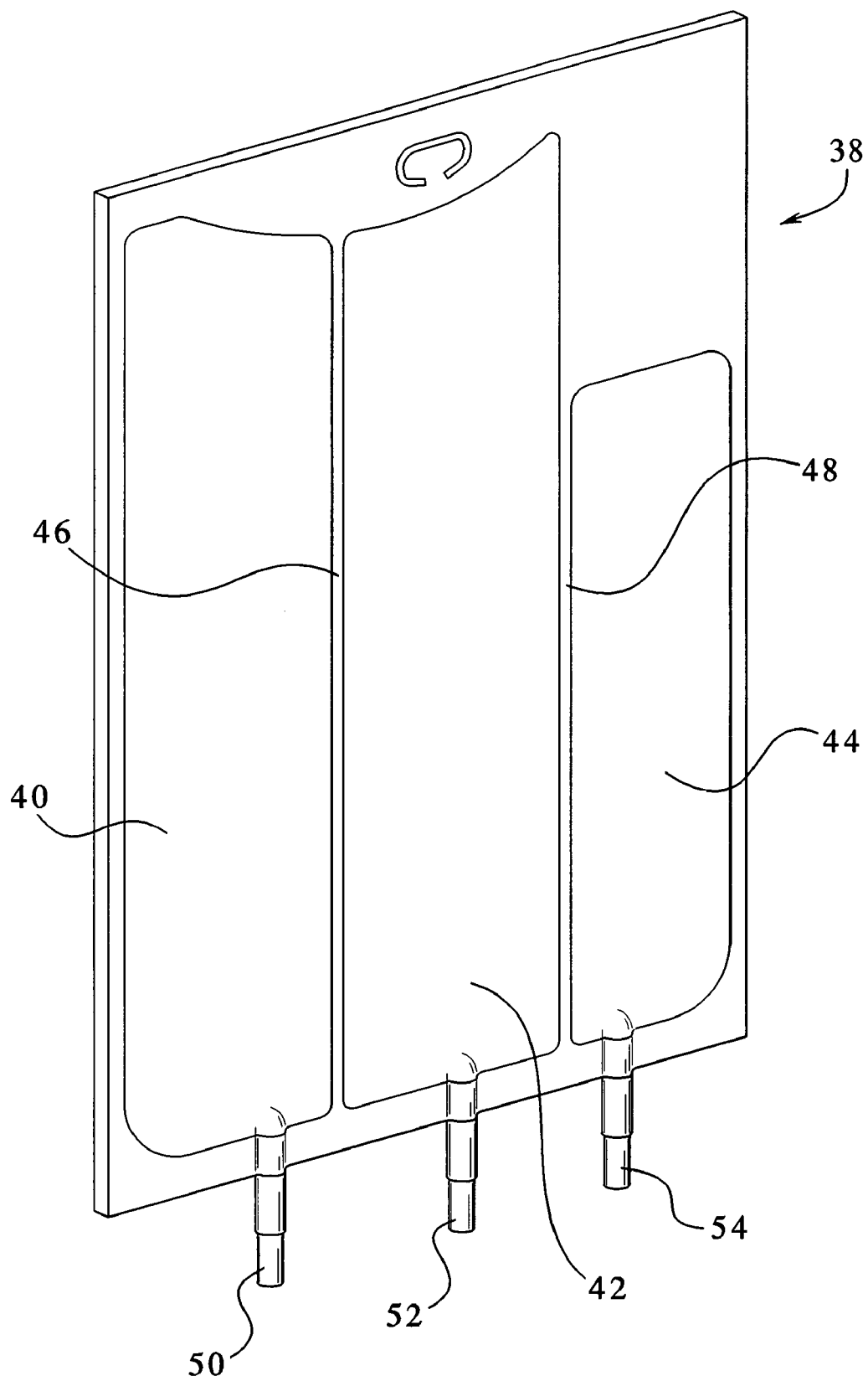
FIG. 12 illustrates a multiple chamber solution bag with a peel seal that contains a multi-part dialysis solution with a therapeutic composition according to an embodiment of the present invention.

In an embodiment, the container can be divided into separate chambers, such as two or more chambers, by a peel seal. With the use of a peel seal, a frangible connector or other suitable type of connector would not be required to mix the solution components within the multi-chamber bag. An example of a multi-chamber solution bag that includes a peel seal is disclosed in U.S. Pat. No. 6,319,243, the disclosure of which is herein incorporated by reference. As shown in FIG. 12, a container 38 includes at least three chambers 40, 42 and 44. The chambers 40, 42 and 44 are designed for the separate storage of liquids and/or solutions, that can be mixed within the container to form a mixed solution ready-for-use. It should be appreciated that more or less than three chambers can be utilized.

The peelable seals 46 and 48 are provided between the chambers 40, 42 and 44, respectively. Examples of peelable seals can be found in U.S. patent application Ser. No. 08/033,233 filed on Mar. 16, 1993 entitled "PEELABLE SEAL AND CONTAINER HAVING SAME", the disclosure of which is herein incorporated by reference. The peelable seals allow for the selective opening of the chambers to allow for the selective mixing of the liquids contained therein.

The container 38 can also include tubular ports, such as tubular ports 50, 52 and 54 as shown in FIG. 12. The tubular ports are mounted to the container so as to allow fluid communication with the container and specifically with chambers 40, 42 and 44. To this end, the tubular ports 50, 52 and 54 can include a membrane that is pierced, for example, by a cannula or a spike or an administration set for delivery of the contents of the container to the patient. It should be appreciated that more or less than three ports can be utilized.

It should be appreciated that the multi-chamber bag can be manufactured from a variety of different and suitable materials and configured in a number of suitable ways such that the dialysis solutions of the present invention can be effectively formulated and administered to the patient during medical therapy in any suitable manner. For example, the first chamber can be larger in volume than the second chamber and further adapted such that the dialysis solution of the present invention can be readily and effectively made and administered to the patient.

As previously discussed, the therapeutic compositions can be added to the dialysis solutions in an effective amount such that the compositions can be effectively utilized during dialysis therapy. In an embodiment, the dialysis solution is contained and administered from a multi-chamber solution bag during peritoneal dialysis, such as during CAPD. The solution bag can include multiple chambers that each contain separate components of the dialysis solution prior to mixing as discussed above. This may be necessary to maintain separation of the non-compatible solution components prior to mixing for purposes of stability, sterility, effectiveness or the like associated with the dialysis solution prior to use. It should be appreciated that the therapeutic compositions can be added to at least one of the solution components prior to mixing. Alternatively, the solution components can be mixed to form the mixed solution wherein the therapeutic composition is added to the mixed solution prior to use.

Figure 13:
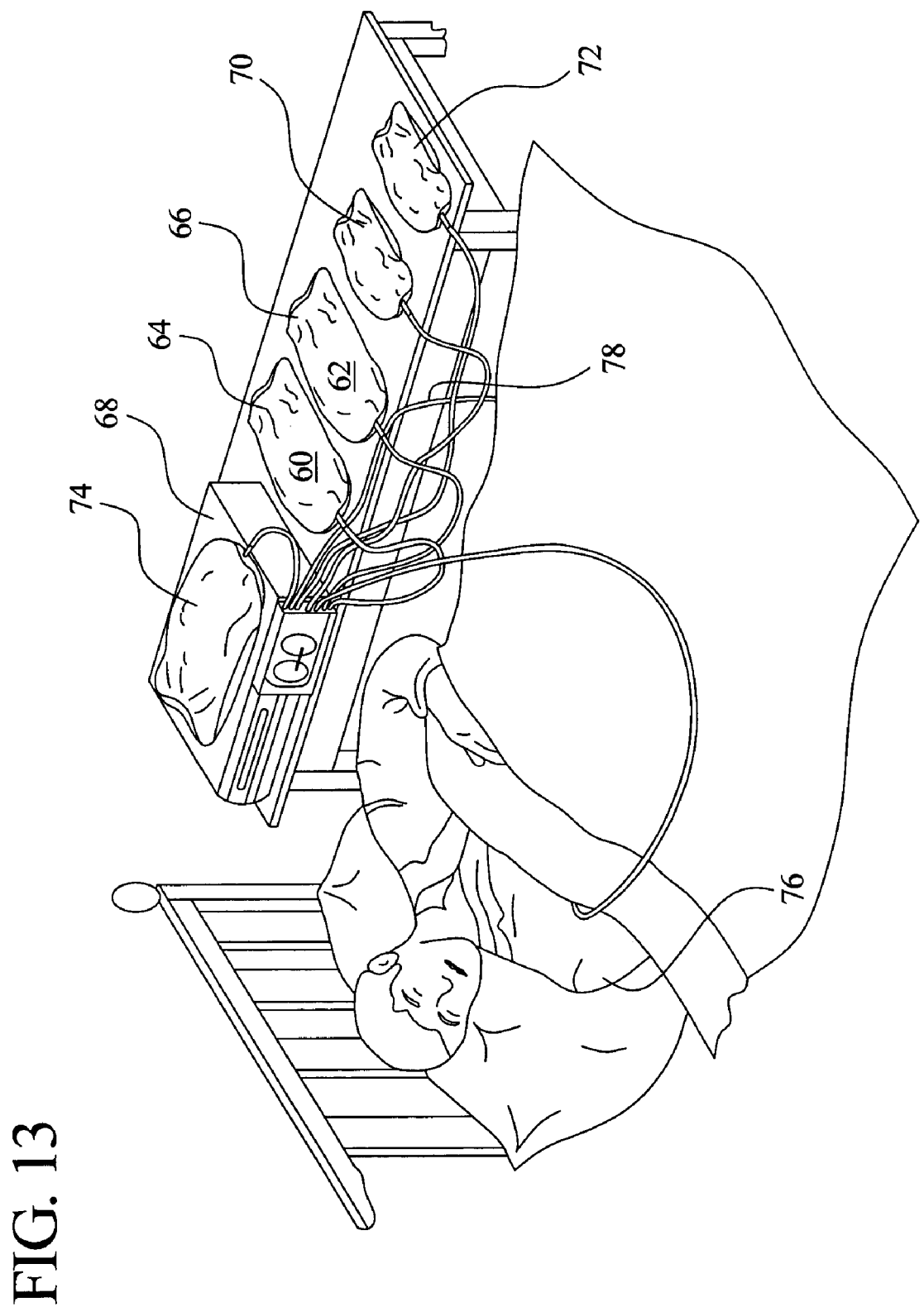
FIG. 13 illustrates a method of performing dialysis according to an embodiment of the present invention.

In another embodiment, the solution components can be prepared and stored in separate containers and then mixed via an admix device prior to use, such as applied during automated peritoneal dialysis. As shown in FIG. 13, a first solution component, such as a dextrose concentrate 60 and a second solution component, such as a buffer concentrate 62 are stored in the respective separate containers 64 and 66 or bags which are fluidly connected to an admix device 68 suitable for use during automated peritoneal dialysis. In addition to the first and second components, a first bag 70 and last bag 72 filled with a suitable solution can also be used during dialysis therapy as generally known.

In an embodiment, an effective amount of the first solution component 60 and the second solution component 62 are drawn from each respective container and into a heater bag 74 where the solution components (e.g., dextrose and buffer concentrates) can be mixed and heated prior to infusion into a patient 76 during dialysis therapy. As further shown in FIG. 13, a drain line 78 is coupled to the admix device 68 from which waste fluids can be removed from the patient during therapy.

Figure 15:
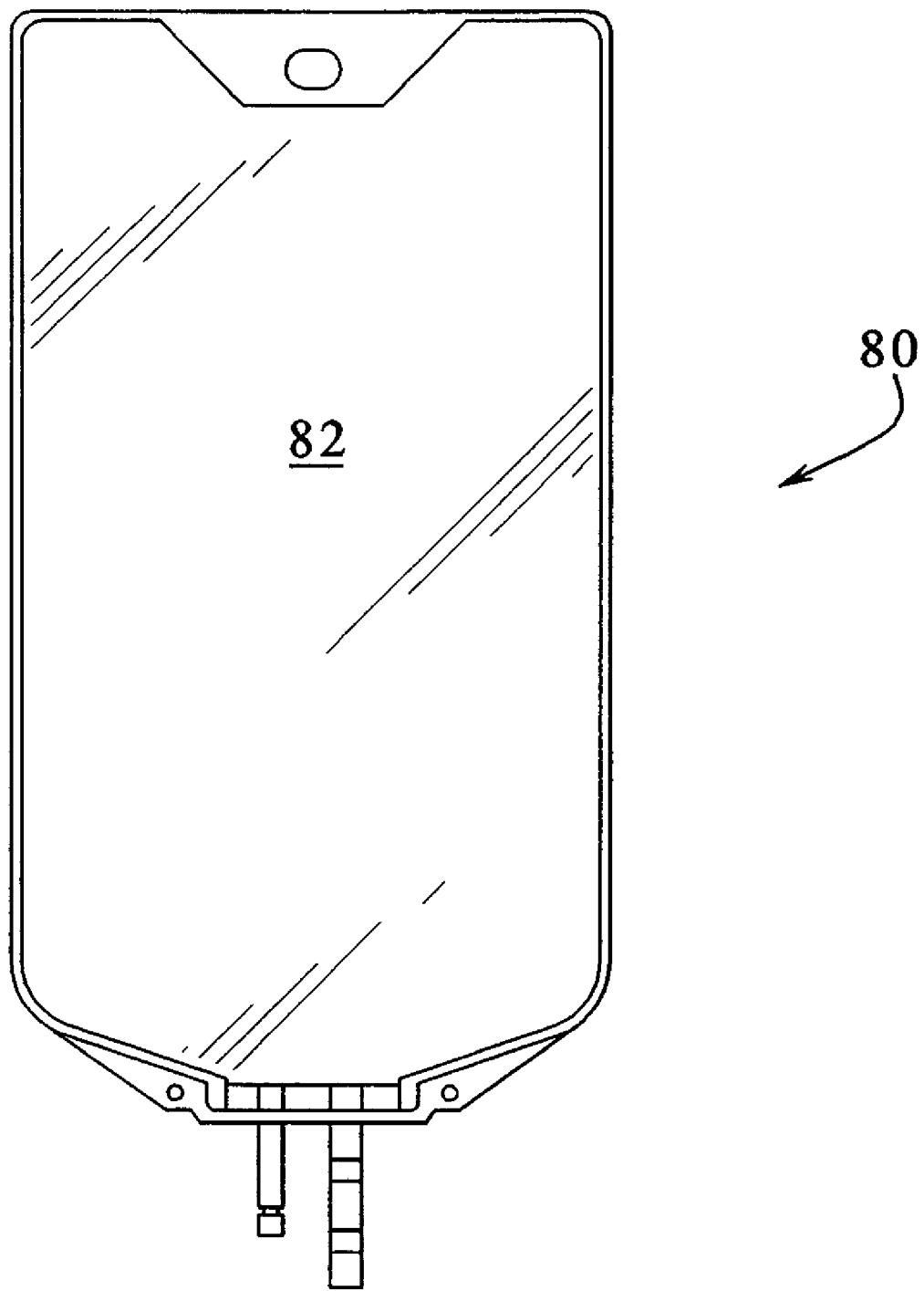
FIG. 15 illustrates a single chamber container with the composition in solution form according to an embodiment of the present invention.

In an embodiment, the compositions of the present invention are additives that can be added to the dialysis solutions at any suitable stage during manufacturing thereof. For example, the additive compositions can be combined within any suitable solution part, alone or in combination with other suitable ingredients, and then mixed and further processed to form a ready-to-use solution. In an embodiment, the additive compositions can be added to a commercially available solution, such as DIANEAL, EXTRANEAL, NUTRINEAL and PHYSIONEAL sold by BAXTER HEALTHCARE CORPORATION. In this regard, the additive compositions can be added directly to the commercially available solution that is contained within a container effectively without altering any other formulation details. The container can include a single chamber container 80 as illustrated in FIG. 15 wherein the dialysis solution 82 is contained, such as a commercially available solution. The additive composition can also be added to one or more solution parts that are contained within a multi-chambered container as discussed above.

The therapeutic compositions of the present invention can be utilized in a number of different and suitable applications. As discussed above, the compositions of the present invention display both effective antioxidant and carboxyl trapping characteristics. In this regard, the present invention can be effectively utilized to reduce systemic inflammation and thus treat inflammatory disease. The therapeutic compositions can be administered in any suitable manner to produce such effect including, for example, oral, intravenous, intramuscular, subcutaneous and/or the like.

The compositions of the present invention can be made and used in any suitable form. For example, the compositions can be provided in solution form as previously discussed. However, it should be appreciated that the compositions can be provided in any suitable form, such as an orally administered product including a pill, a tablet, a capsule, a powder, a film, a solution and the like. The orally administered product can be made with any suitable carrier.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A composition comprising a single molecule that is capable of inhibiting a reactive oxygen species and a reactive carbonyl species, the single molecule comprising an antioxidant moiety, a carbonyl trapping moiety and a linker moiety that joins the antioxidant moiety and the carbonyl trapping moiety, wherein the antioxidant moiety is selected from the group consisting of vitamin E, cinnamic acid derivatives, pyridoxamine, flavonoids, lipoic acid, antioxidants including natural antioxidants and synthetic antioxidants, derivatives thereof, and combinations thereof, wherein the carbonyl trapping moiety is selected from the group consisting of an aminooxy group, a 1,2-aminothiol group including a cysteine group, a penicillamine group, derivatives thereof, and combinations thereof and wherein the linker moiety is selected from the group consisting of piperazine, poly(ethylene glycol), lysine, an organic moiety containing a positive charge, an organic moiety containing a negative charge, an organic moiety containing a positive charge and a negative charge, derivatives thereof, and combinations thereof.

2. A composition comprising a single molecule that is capable of inhibiting a reactive oxygen species and a reactive carbonyl species, wherein the single molecule includes a vitamin E derivative selected from the group consisting of 2-(6-hydroxy-2,5,7,8-tetramethylchroman-2-yl)-1-(aminooxy)ethane; N-[2-(6-hydroxy-2,5,7,8-tetramethylchroman-2-yl)ethyl]-N'-(aminooxyacetyl)-piperazine; N-[2-(6-hydroxy-tetramethylchroman-2-yl)ethyl]-N'-(cysteinyl)-piperazine; N-[2-(6-hydroxy-tetramethylchroman-2-yl)ethyl]-N'-(penicillamyl)-piperazine, derivatives thereof, and combinations thereof.

3. A dialysis solution comprising a therapeutically effective amount of a composition capable of inhibiting a reactive oxygen species and a reactive carbonyl species, the composition comprising a single molecule comprising an antioxidant moiety, a carbonyl trapping moiety, and a linker moiety that joins the antioxidant moiety and the carbonyl trapping moiety, wherein the antioxidant moiety is selected from the group consisting of vitamin E, cinnamic acid derivatives, pyridoxamine, flavonoids, lipoic acid, antioxidants including natural antioxidants and synthetic antioxidants, derivatives thereof, and combinations thereof, wherein the carbonyl trapping moiety is selected from the group consisting of an aminooxy group, a 1,2-aminothiol group including a cysteine group, a penicillamine group, derivatives thereof, and combinations thereof and wherein the linker moiety is selected from the group consisting of piperazine, poly(ethylene glycol), lysine, an organic moiety containing a positive charge, an organic moiety containing a negative charge, an organic moiety containing a positive charge and a negative charge, derivatives thereof, and combinations thereof.

4. A two part peritoneal dialysis solution comprising:
a first part including an osmotic agent; and
a second part including a buffer, wherein the first part and the second part are admixed prior to use, and wherein at least one of the first part and the second part includes a therapeutically effective amount of a composition capable of inhibiting a reactive carbonyl species and a reactive oxygen species, the composition comprising a single molecule comprising an antioxidant moiety, a carbonyl trapping moiety, and a linker moiety that joins the antioxidant moiety and the carbonyl trapping moiety, wherein the antioxidant moiety is selected from the group consisting of vitamin E, cinnamic acid derivatives, pyridoxamine, flavonoids, lipoic acid, antioxidants including natural antioxidants and synthetic antioxidants, derivatives thereof, and combinations thereof, wherein the carbonyl trapping moiety is selected from the group consisting of an aminooxy group, a 1,2-aminothiol group including a cysteine group, a penicillamine group, derivatives thereof, and combinations thereof and wherein the linker moiety is selected from the group consisting of piperazine, poly (ethylene glycol), lysine, an organic moiety containing a positive charge, an organic moiety containing a negative charge, an organic moiety containing a positive charge and a negative charge, derivatives thereof, and combinations thereof.

5. A method of providing dialysis to a patient, the method comprising:
providing a dialysis solution including a therapeutically effective amount of a composition that is capable of inhibiting a reactive oxygen species and a reactive carbonyl species, the composition comprising a single molecule comprising an antioxidant moiety, a carbonyl trapping moiety, and a linker moiety that joins the antioxidant moiety and the carbonyl trapping moiety, wherein the antioxidant moiety is selected from the group consisting of vitamin E, cinnamic acid derivatives, pyridoxamine, flavonoids, lipoic acid, antioxidants including natural antioxidants and synthetic antioxidants, derivatives thereof, and combinations thereof, wherein the carbonyl trapping moiety is selected from the group consisting of an aminooxy group, a 1,2-aminothiol group including a cysteine group, a penicillamine group, derivatives thereof, and combinations thereof and wherein the linker moiety is selected from the group consisting of piperazine, poly(ethylene glycol), lysine, an organic moiety containing a positive charge, an organic moiety containing a negative charge, an organic moiety containing a positive charge and a negative charge, derivatives thereof, and combinations thereof; and using the dialysis solution during dialysis.

6. A method of reducing inflammation and oxidative stress in a kidney disease patient, the method comprising:

providing a dialysis solution including a therapeutically effective amount of a composition that is capable of inhibiting a reactive oxygen species and a reactive carbonyl species, the composition comprising a single molecule comprising an antioxidant moiety, a carbonyl trapping moiety, and a linker moiety that joins the antioxidant moiety and the carbonyl trapping moiety and wherein the antioxidant moiety is selected from the group consisting of vitamin E, cinnamic acid derivatives, pyridoxamine, flavonoids, lipoic acid, antioxidants, derivatives thereof, and combinations thereof; wherein the carbonyl trapping moiety is selected from the group consisting of an aminooxy group, a 1,2-aminothiol group including a cysteine group, a penicillamine group, derivatives thereof and combinations thereof; and wherein the linker moiety is selected from the group consisting of piperazine, poly(ethylene glycol), lysine, derivatives thereof, and combinations thereof; and using the dialysis solution to administer dialysis to the patient.

* * * * *